United States Patent [19]

Chadwick et al.

[11] Patent Number: 5,131,755
[45] Date of Patent: * Jul. 21, 1992

[54] AUTOMATIC HIGH SPEED OPTICAL INSPECTION SYSTEM

[76] Inventors: Curt H. Chadwick, 220 Wooded View Rd., Los Gatos, Calif. 95032; Robert R. Sholes, 170 Middlefield Rd., Boulder Creek, Calif. 95006; John D. Greene, 2275-6 Kinsley St., Santa Cruz, Calif. 95062; Francis D. Tucker, III, 2809 Tramanto Dr., San Carlos, Calif. 94070; Michael E. Fein, 1909 Limetree La., Mountain View, Calif. 94040; P. C. Jann, 2360 Warburton Ave., Santa Clara, Calif. 95050; David J. Harvey, 425 Dallas Dr., Campbell, Calif. 95008; William Bell, 685 Estonia Ct., San Jose, Calif. 95123

[*] Notice: The portion of the term of this patent subsequent to Oct. 31, 2006 has been disclaimed.

[21] Appl. No.: 429,859

[22] Filed: Oct. 31, 1989

Related U.S. Application Data

[63] Continuation-in-part of Ser. No. 158,289, Feb. 19, 1989, Pat. No. 4,877,326.

[51] Int. Cl.$^5$ .............................................. G01B 11/30
[52] U.S. Cl. ..................... 356/394; 356/386; 356/446
[58] Field of Search ............... 356/237, 386, 387, 394, 356/398, 446, 448; 358/101, 106, 107; 396/398

[56] References Cited

U.S. PATENT DOCUMENTS

| | | | |
|---|---|---|---|
| 3,909,602 | 9/1975 | Micka | 356/394 |
| 3,963,354 | 6/1976 | Feldman et al. | 356/394 |
| 4,680,627 | 7/1987 | Sase et al. | 356/394 |
| 4,799,175 | 1/1989 | Sano et al. | 356/394 |
| 4,877,326 | 10/1989 | Chadwick et al. | 356/446 |

Primary Examiner—Samuel Turner
Attorney, Agent, or Firm—Allston L. Jones

[57] ABSTRACT

In each configuration, at least one TDI sensor is used to image substrate portions of interest, with those portions illuminated with substantially uniform illumination. In one configuration, a substrate is compared to prestored expected characteristic features. In a second configuration, first and second patterns in a region of the surface of at least one substrate are inspected by comparing one pattern against the other and noting whether they agree with each other. This is accomplished by illuminating the two patterns, imaging the first pattern and storing its characteristics in a temporary memory, then imaging the second pattern and comparing it to the stored characteristics from the temporary memory. Then the comparisons continue sequentially with the second pattern becoming the first pattern in the next imaging/comparison sequence against a new second pattern. Each time the comparison is performed, it is noted whether or not there has been agreement between the two patterns and which two patterns where compared. This inspection technique is useful for doing die-to-die inspections. A variation of the second configuration uses two TDI sensors to simultaneously image the first and second patterns, thus eliminating the need for temporary memory. In this configuration, the two patterns are simultaneously imaged and compared, then additional patterns are compared sequentially, in the same manner with the results of the comparisons and the pattern locations stored to determine which patterns are bad when the inspection of all patterns is completed.

12 Claims, 27 Drawing Sheets

Condition 1: Low NA, no slit
— Insulator Peak
— Conductor Peak

Condition 2: High NA, no slit
— Conductor Peak
— Insulator Peak

Condition 3: High NA with slit
— Conductor Peak
— Insulator Peak

Intensity of reflected light ⟶

Transmission Spectrum for Dupont Riston® 215R Photoresist

CASE 1 SPEC: $M_{VLC} = \dfrac{R_{CP} - R_D}{R_L - R_D} \geq .6$

CASE 2
VERTICAL LIGHT
LINE CENTERED
ON A BOUNDARY
BETWEEN COLUMNS

CASE 2 SPEC: $M_{VLB} = \dfrac{R_{CP} - R_D}{R_L - R_D} \geq .4$

CASE 3
VERTICAL DARK
LINE CENTERED
ON A COLUMN

CASE 3 SPEC: $M_{VDC} = \dfrac{R_L - R_{CP}}{R_L - R_D} \geq .6$

CASE 4
VERTICAL DARK
LINE CENTERED
ON A BOUNDARY
BETWEEN COLUMNS

CASE 4 SPEC: $M_{VDB} = \dfrac{R_L - R_{CP}}{R_L - R_D} \geq .4$

CASE 5 SPEC: $M_{HLC} = \dfrac{R_{CP} - R_D}{R_L - R_D} \geq .6$

CASE 6 SPEC: $M_{HLB} = \dfrac{R_{CP} - R_D}{R_L - R_D} \geq .4$

CASE 6 SPEC: $M_{HDC} = \dfrac{R_L - R_{CP}}{R_L - R_D} \geq .6$

CASE 8
HORIZONTAL DARK LINE CENTERED ON A BOUNDARY BETWEEN ROWS

CASE 8 SPEC: $M_{HDB} = \dfrac{R_L - R_{CP}}{R_L - R_D} \geq .4$

Pixel Size / Scan Speed Decode For PLL
$S_H$ = PXS21  PXS20  SPD1  SPD0

| $S_H$ | Pixel Size | Scan Speed | Encoder Multiply | Feedback Divide | Output Divide | 4XCK | PIXCLK | Tach Clock |
|---|---|---|---|---|---|---|---|---|
| 0 | 6.5 μm | 3.05 ips | 4 | 1760 | 4 | 6.8 MHz | 1.7 MHz | .5 MHz |
| 1 | 6.5 | 6.1 | 2 | 1760 | 2 | 13.6 | 3.4 | 1.0 |
| 2 | 6.5 | 12.2 | 2 | 880 | 1 | 27.3 | 6.8 | 2.0 |
| 3 N/A | 6.5 | 24.4 | 1 | 880 | — | — | — | 4.0 |
| 4 | 13 | 3.05 | 4 | 1760 | 8 | 3.4 | .85 | .5 |
| 5 | 13 | 6.1 | 2 | 1760 | 4 | 6.8 | 1.7 | 1.0 |
| 6 | 13 | 12.2 | 2 | 880 | 2 | 13.6 | 3.4 | 2.0 |
| 7 | 13 | 24.4 | 1 | 880 | 1 | 27.3 | 6.8 | 4.0 |
| 8 | 26 | 3.05 | 4 | 1760 | 16 | 1.7 | .42 | .5 |
| 9 | 26 | 6.1 | 2 | 1760 | 8 | 3.4 | .85 | 1.0 |
| A | 26 | 12.2 | 2 | 880 | 4 | 6.8 | 1.7 | 2.0 |
| B | 26 | 24.4 | 1 | 880 | 2 | 13.6 | 3.4 | 4.0 |
| C N/A | — | 3.05 | 4 | 1760 | — | — | — | .5 |
| D N/A | — | 6.1 | 2 | 1760 | — | — | — | 1.0 |
| E N/A | — | 12.2 | 2 | 880 | — | — | — | 2.0 |
| F N/A | — | 24.4 | 1 | 880 | — | — | — | 4.0 |

Fig. 28

AUTOMATIC HIGH SPEED OPTICAL INSPECTION SYSTEM

CROSS REFERENCE

This application is a continuation in part application of patent application entitled "Automatic High Speed Optical Inspection System" filed on Feb. 19, 1988, given Ser. No. 158,289, and now U.S. Pat. No. 4,877,326 assigned to the same assignee as the present application.

BACKGROUND OF THE INVENTION

The present invention relates to automated inspection of surfaces such as printed wiring boards and the like, and more particularly to the automated high speed inspection of surfaces using a TDI sensor as a detector.

A printed wiring board (pwb) comprises a pattern of electrical conductors (made of a material such as 1.4-mil-thich copper) residing on a non-conducting substrate (made of a material such as FR-4 epoxy-fibergalss composite). During the manufacture of pwb's, the top surface of the conductive material is often intentionally roughened, in order to promote adhesion of photoresist to the conductor. Among the methods of roughening are mechanical abrasion, chemical etching, and application of a textured surface layer by electroplating (as in so-called "double-treat copper"). Each roughening method produces its own characteristic surface texture.

It is therefore a requirement, in the design of a machine for the optical inspection of pwb's that the machine is able to cope effectively with a wide variety of surface textures. It is also desirable, in order that the machine be as flexible in application as possible, that it be able to correctly inspect pwb's in which the conductors have smooth surfaces.

The most common and straightforward may to illuminate opaque optical surfaces for inspection is to provide illumination through the same lens that will be used to view the inspected surface, and to collect with that lens the light which is reflected or scattered from the surface. This method is commonly known as brightfield vertical illumination, or simply as brightfield illumination.

FIG. 2 illustrates the problem which is inherent in using brightfield illumination to inspect pwbs. A copper conductor 8 (shown in cross-section) resides on an insulating substrate 9. The top surface of conductor 8 is shown to be rough (the characteristic dimension of the roughness is greatly exaggerated for illustrative purposes). Illumination is provided through lens 11, which is also used for viewing light reflected or scattered from the surface.

Consider now the behavior of this system in inspecting a particular point 13 on the conductor surface. Point 13 has been selected, for illustrative purposes, to be within a small area that is sloped substantially away from level. Illumination rays 1 and 2 arrive at point 13 from the extreme edges of lens 11. All other light rays 1 and 2. The inclination of the surface at point 13 is such that ray 1 is reflected into ray 3, and ray 2 is reflected into ray 4, both of these rays lying outside the aperture of lens 11. All other illumination rays will reflect somewhere between ray 3 and ray 4, which is to say that none of the illuminating light will be reflected back into lens 11. Any optical sensor that is placed above lens 11, so as to view the returning rays, will see point 13 as being black, because none of the light leaving point 13 gets through the lens.

The general point being illustrated here is that when a rough surface is viewed by brightfield vertical illumination, the steeply inclined portions of that surface will tend to appear dark, and the overall appearance of the surface will be strongly mottled.

It is necessary for the optical inspection machine to distinguish between regions of copper and regions of insulator. This is often done by taking advantage of the fact that conductive regions are more reflective than are insulating regions, at least at selected wavelengths. Electronic logic can be employed which identifies dark regions as being insulative and bright regions as being conductive. If an optical illumination system causes conductive regions to appear mottled, then some parts of the conductive regions will be falsely identified as being insulative.

A known cure for this problem is to average observed reflectance values over a relatively large region, so as to take advantage of the fact that the average reflectance, even of rough-textured copper, is often higher than the average reflectance of substrate materials. This method has the disadvantage, however, that it makes it impractical to detect actual missing-copper defects of a size smaller than the averaging region.

Defining Numerical Aperture (NA) of the illuminator in the conventional way, which is to say that NA = sin ($\theta$), $\theta$ being the angle between a normal to the surface and the extreme illuminating ray, the NA of illumination should be at least about 0.7 NA, and preferable greater than 0.8 NA. In addition, the illumination should be of constant intensity (watts/steradian/cm$^2$) over all angles of incidence (i.e. quasi-Lambertian).

An achievement of the present invention is that, be reducing optically the apparent mottling of rough-textured surfaces, it is made possible to avoid large-area averaging, and consequently it becomes possible to detect smaller regions of missing conductive material.

It is not new to provide focussed illumination from a large range of angles, up to a numerical aperture which may even exceed 0.9. Such illumination is achieved, for example, in brightfield vertical illuminators used in high-magnification microscopes employing high-NA objectives. The best of such microscopes achieve illumination NA's on the order of 0.95. The intensity of illumination in such microscopes is not, however, independent of the angle of incidence. The falloff in transmission of strongly-curved lens elements at large angles causes the illumination provided by such objectives to be significantly weaker at angles far from the normal.

SUMMARY OF THE INVENTION

In accordance with the illustrated embodiments, the present invention presents methods and apparatus for inspecting surface features of a substrate. In each configuration, at least one TDI sensor is used to image the portions of interest of the substrate, with those portions illuminated with substantially uniform illumination.

A first embodiment checks the substrate against the characteristic features of the substrate being inspected against prestored characteristics from a memory means. Then, as the substrate being inspected is imaged, that image is compared against the stored characteristics from the memory means.

In a second embodiment, a first and second pattern in a region of the surface of at least one substrate are to be inspected by comparing one pattern against the other and noting whether they agree with each other without the prestoring of an expected pattern. This accomplished by illuminating at least the two patterns, imaging the first pattern and storing its characteristics in a temporary memory, then imaging the second pattern and comparing it to the stored characteristics from the temporary memory. Here, the comparison reveals whether the two patterns agree or not. Then the comparisons continue sequentially with the second pattern becoming the first pattern in the next imaging/comparison sequence against a new second pattern. Each time the comparison is performed, it is noted whether or not there has been agreement between the two patterns and which two patterns where compared. After all of the patterns are sequentially compared, the bad ones are identified by identifying those that did not compare with other patterns in the test process. This inspection technique is useful for doing die-to-die inspections.

The third embodiment is similar to the second embodiment. In this embodiment, two TDI sensors are used to simultaneously image the first and second patterns, thus eliminating the need for the temporary memory. In this embodiment, the two patterns are simultaneous imaged and compared, then additional patterns are compared sequentially, in the same manner with the results of the comparisons and the pattern locations stored determine which patterns are bad when the inspection of all patterns is completed.

BRIEF DESCRIPTION OF THE FIGURES

FIG. 28 is a table that describes the frequency of the output clock for each combination of pixel size and scan speed.

DESCRIPTION OF THE PREFERRED EMBODIMENTS

System Overview

Figure 1:
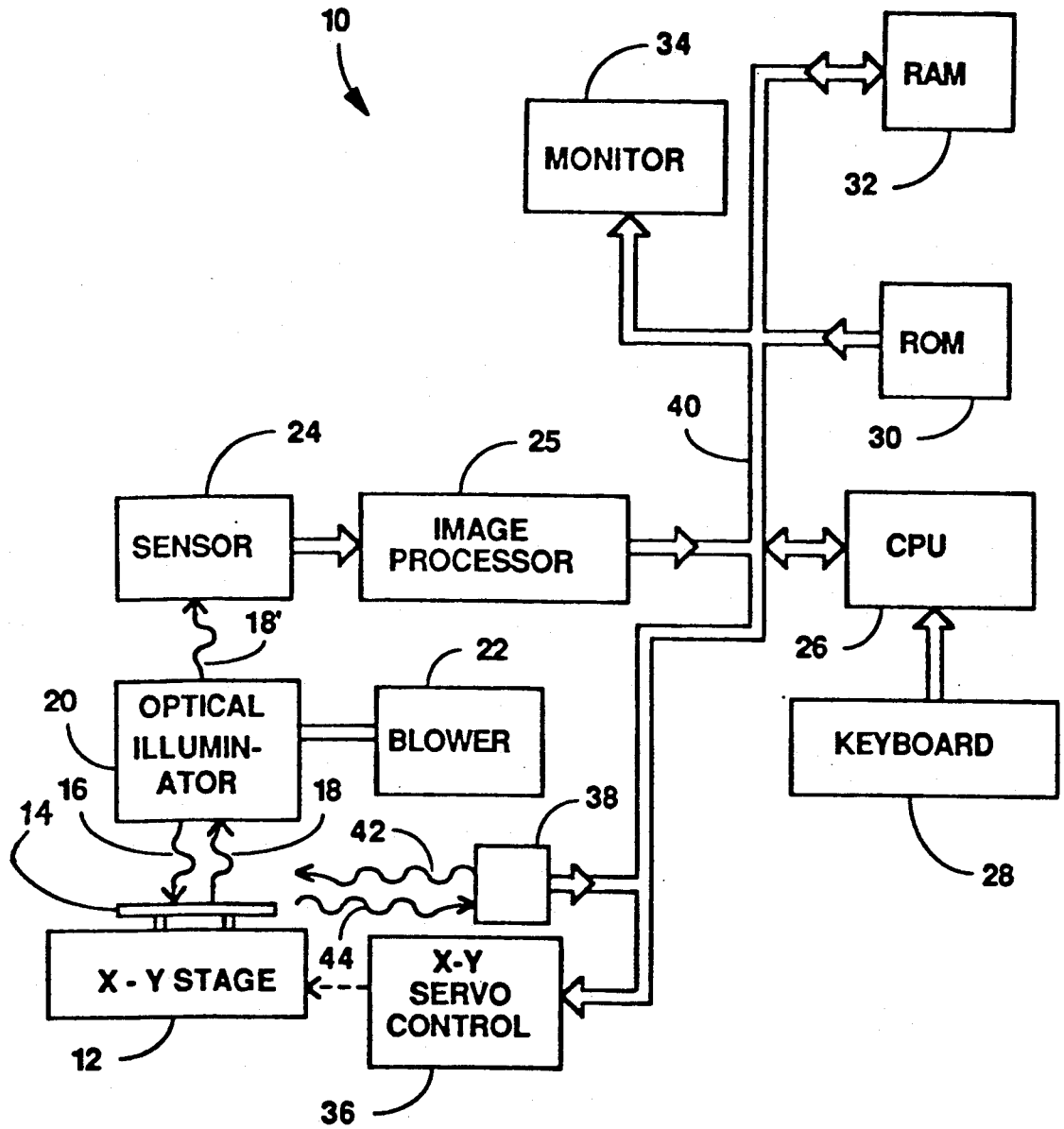
FIG. 1 is a block diagram of the automatic printed wiring board inspection machine of the present invention.

In FIG. 1 there is shown an overall block diagram for the inspection system 10 of the present invention. In system 10 the method of testing is basically the comparison of the surface of a first substrate the surface of a second substrate that is intended to be the same as the first substrate (die-to-die), or the basic characteristics of the expected pattern of the substrate being inspected stored in memory (data base).

The first of the configurations, die-to-die, is useful when the substrate, say a semiconductor wafer, includes a plurality of dies which are intended to be the same as each other. In this situation two dies are viewed simultaneously with the feature of one compared to those of the other. If there is a discrepancy, the discrepancy is noted and between which two dies that discrepancy exists. The process continues with each die being viewed twice with the possible exceptions of the first and last dies in an inspection path. With this method of inspection the bad dies can be singled out since they will generally show up in more than one non-comparing pair. In this inspection mode none of the expected characteristics of each die are stored in a data base from any source. This method could also be used when the "dies" are separate, e.g. two or more printed circuit boards. In the execution of the actual examination there is a choice of performing the inspection with a matched pair of optical paths and sensors with sensor output signals applied simultaneously to the comparator, or with a single optical path and sensor with the image characteristics of the first die stored temporarily and then applied to the comparator as the second die is imaged. The image characteristics of the second die then overwrite those of the first die in the temporary memory and the process continues as discussed above.

In the data base configuration, the image characteristics of the substrate to be inspected are pre-stored in memory with the data being generated other than by optical imaging of a known good substrate, or "golden board". The most common way that such a data base is generated is by a CAD system from which the substrate was originally designed. Such a data base can also be manually generated which, for most applications, would be very inefficient. In operation, this configuration would then optically image the substrate being inspected and compare the imaged characteristics with those stored in the data base. Here, a non-comparing substrate is automatically identified as defective.

The applicants' application of the system herein disclosed is the inspection of wafers, masks, printed wiring boards, photo tools, and the like.

System 10 in the embodiment of the present invention is a computer controlled system having a CPU 26 that communicates with various other elements of the system via data bus 40. The other elements of the system coupled to data bus 40 are ROM 30, RAM 32, monitor 34, X-Y servo control 36, location sensors 38, and image processor 25. Keyboard 28 is provided for user interaction with the system to initiate and manually control inspection of the substrate 14, and monitor 34 is provided for visual feedback to the user of the area of substrate 14 that is currently being viewed. RAM 32 and ROM 30 are included for the usual functions in a CPU controlled system. X-Y servo control 36 is mechanically linked to one or more X-Y stages 12 to more substrates 14 to the desired location under CPU 26 control. Location sensors 38 are linear scales for determining the X and Y position of stages 12. Mounted directly above substrate 14 is optical illuminator 20 which provides illumination to the surface of substrates 14 by light rays 16, and through which the surface of the substrate is viewed by light rays 18 and 18' by sensors 20. Sensors 20 convert the viewed image of the surface of substrates 14 to an electrical signal that is applied to image processor 25. Image processor 25 in turn operates on the signals from sensors 24 to both enhance the detected image and to restructure the data to compress it to minimize the memory necessary to store the received data in RAM 32 depending on which mode of operation is being employed.

In operation in the data base mode, the user initially stores in RAM 32 the design characteristics of the pattern on the surface of the substrate 14 to be inspected. Those characteristics include location and characteristics of features and connectivity information. This can be done with the database used to generate the pattern.

Through the use of various illumination techniques discussed below in combination with a selected image sensor, e.g. a TDI sensor, the surface of substrates, such a printed wiring boards, can be inspected with the substrate traversing in a straight line beneath the illuminator at speeds in the range of 25 inches per second.

Optical Illuminator

One of the embodiments of the present invention is an illumination apparatus which, to the greatest extent possible, provides a uniform sky of illumination above the workpiece being inspected, so as maximally to suppress texture-induced mottling effects.

Figure 2:
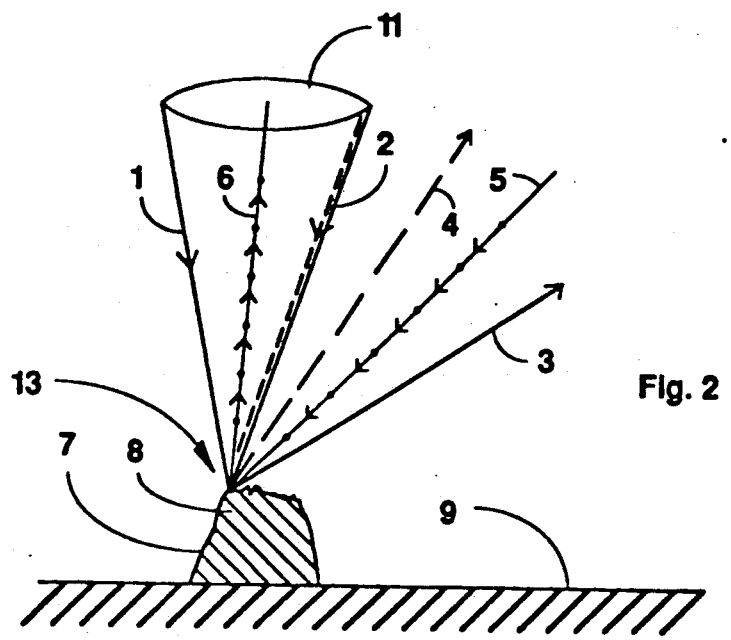
FIG. 2 is cross sectional view that illustrates the light scattering effect of a representative copper trace on a printed wiring board to be inspected.

Optical illuminator 20 may be understood by considering illumination ray 5, in FIG. 2. This ray is provided by an illumination system (not shown), from an angle outside the aperture of lens 22. Ray 5 is reflected by the inclined surface at point 13, to become ray 6, which enters lens 11. This ray, when imaged on a sensor, will contribute to making the surface region around point 13 appear bright rather than dark. The reasoning exemplified by this discussion of FIG. 2 led to proving that the mottled appearance of rough surfaces can be markedly reduced or even eliminated, by providing illuminating light rays from a great many angles, so that whatever the local inclination of a particular region of the surface, there will always be illuminating rays available at the appropriate angles to be reflected into the viewing lens.

For each angle at which an element of surface may be sloped, there will be a particular group of illuminating rays that will be reflected from that surface into the viewing lens. In order that surfaces sloped at different angles may appear to the sensor to be equally bright, it is important that all the different groups of rays be of similar intensity. From the standpoint of an imaginary observer, stationed on the conducting surface and looking up, it should appear that light is arriving from all directions with equal intensity; i.e. that the observer stands beneath a sky of uniform brightness.

This illumination condition would pertain if there were a Lambertian diffusing surface, such as a piece of opal glass, located directly above the observer, and if spatially uniform illuminating light were delivered through this surface. A Lambertian surface is one which radiates equal optical power densities into equal solid angles, so that an observer looking at the surface from any direction sees the same brightness. An imaginary observer residing on the workpiece would loop up at the opal-glass sky, and in no matter what direction he looked would see an intensity proportional to the intensity of light striking the top of the opal glass at the point where he was looking. Thus, the spatial uniformity of light striking the top of the opal glass would result in angular uniformity of light as seen at the observation area.

Such an illuminator would be unusable, if for no other reason than that the opal glass would prevent viewing of the object. The illuminator of the present invention is a practical illuminator which approximates the ideal Lambertian illuminator to a useful extent. It can be described as a quasi-Lambertian illuminator.

There are some forms of surface roughness which make total suppression of mottling impossible. This can be understood by considering FIG. 3. Point 205 on the surface of conductor 8 is tilted so far from the horizontal as to be inaccessible to sky illumination. Rays 201 and 202 extend from point 205 to the boundaries of lens 11. Rays 203 and 204 are the illuminating rays which would have to be provided, in order to be reflected into rays 201 and 202. These rays would have to come from within conductor 8, which is not possible, or would have to arrive at point 205 after undergoing one or more reflections from other points on the conductor surface. Since the reflectivity of surface materials is imperfect, indirectly-illuminated points like point 205 will appear to be darker than points that are directly illuminated by the sky.

In spite of the theoretical impossibility of total suppression of mottling, we have observed empirically that the close we come to providing a uniform sky of illumination above the workpiece, the more effectively mottling is suppressed. With optimal suppression of mottling, we can adjust the inspection algorithms to find the smallest possible defects in the conductor pattern, without creating false defects due to incorrect identification of dark copper areas as insulator.

Figure 4:
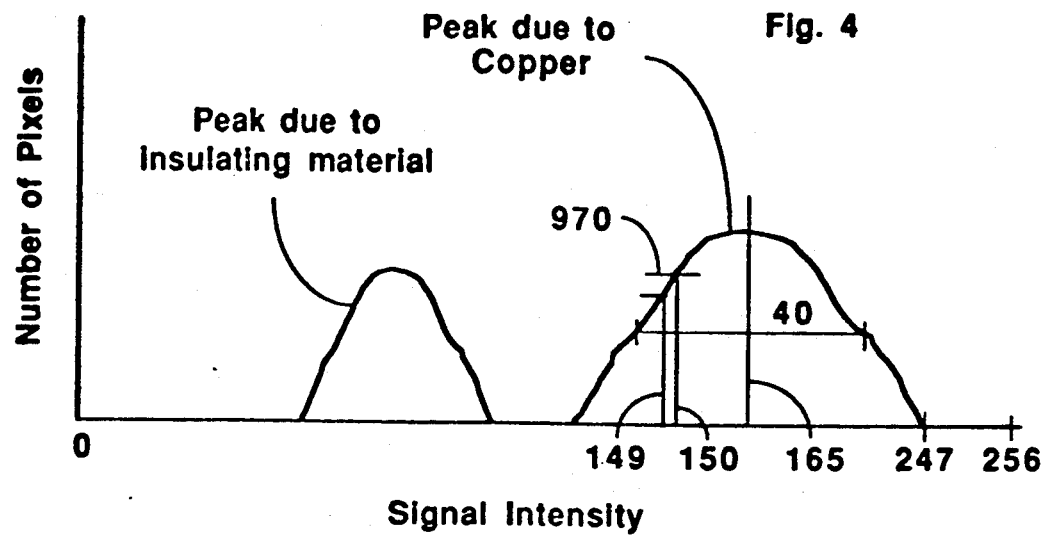
FIG. 4 is a histogram that illustrates the difference in the intensity of the reflected light from a copper trace versus a fiberglass substrate.
Figure 5:
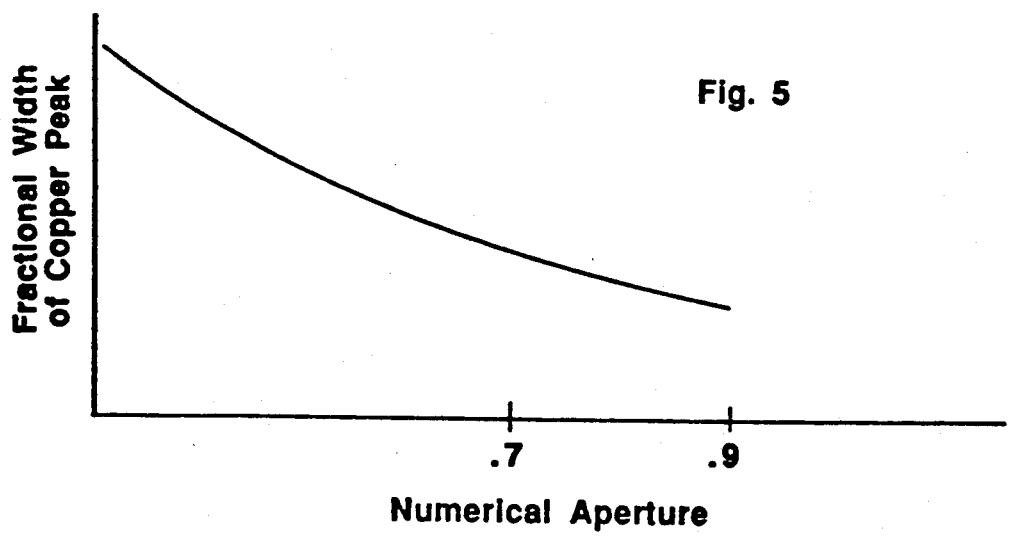
FIG. 5 is a graph that shows the relationship between the width of the copper reflectivity peak and the numerical aperture of the illuminator.

Based on data collected in an experiment using a quasi-Lambertian illuminator, the histogram of FIG. 4 shows the distribution of pixel intensities for areas of the object (a small sample cut from a pwb) which are covered with copper, and another distribution for areas in which the insulating FR4 substrate is exposed. We observed the width of the copper peak, as a fraction of its average value, while varying the numerical aperture of illumination. This function is plotted in FIG. 5.

It can be seen that the peak narrows as the numerical aperture increases, up to the limit of the experiment. The data demonstrate that, from the standpoint of minimizing the apparent surface mottling of rough copper surfaces, it is desirable to have the highest possible numerical aperture of illumination, that numerical aperture exceeding at least 0.7 NA, and preferable exceeding 0.8 NA.

Figure 3:
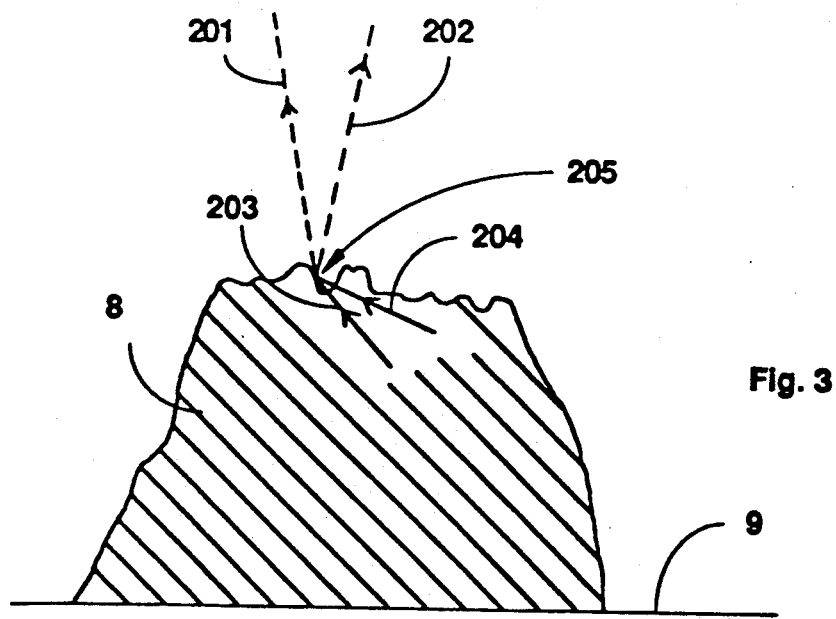
FIG. 3 illustrates a portion of the surface of a copper trace where illumination of the surface is impossible by any illumination scheme.

It should also be understood that, while FIGS. 2 and 3 show cross-sections in which illumination is shown as being uniform in one particular cross-sectional plane, it is desirable to have uniformity in all directions about the object. If this were not done, for example, a small area of surface which was tilted 40 degrees from the normal in a northerly direction would have a different apparent brightness from an elemental surface area tilted in an easterly direction.

The general rule that emerges from the experiments is that every part of the sky must, to the greatest extent possible, be uniformly filled with light, in order to minimize apparent mottling of rough surfaces.

There is an advantage of quasi-Lambertian illumination in addition to the advantage of mottling reduction, which is that such illumination improves the ability of an optical inspection system to find the bottom edges of conductive lines.

Returning to FIG. 2, note that edge 7 of the conductor line is sloped at an angle to the vertical, so that the line has greater width at the bottom than at the top. A common inspection requirement is to determine the gap between adjacent conductors at the bottom since it is at their closest distance of approach that conductors are most likely to be short-circuited. A brightfield illuminator will typically cause an edge like 7 to appear dark, and indistinguishable from the substrate material, because edge 7 will not reflect brightfield rays back into the viewing lens. It is therefore a tendency of brightfield illuminators to cause conductor widths to be measured at the top (since only the to of the conductor can be seen). It can be demonstrated that for many of the varying edge profiles that are seen on pwb's, the use of quasi-Lambertian illumination is helpful in providing rays that make conductor edges visible, so that conductor widths and spacings can be measured at the bottom of the conductor profile.

A general requirement for the illuminator is that the light intensity in the optical field-of-view be substantially uniform along the length (Y direction) of the TDI sensor. However, it need not be uniform in the X direction, the direction of motion of the stage (perpendicular to the long axis of the TDI sensor). This is due to the integrating property of the TDI sensor in that direction. This property allows the light to have any intensity profile in the X-direction, so long as the integrated total energy across the sensor field-of-view is uniform along the length of the field-of-view. This makes the construction of an illuminator for a TDI sensor much easier than for a conventional area sensor that requires substantially constant light in both axes. This integrating property even makes the system tolerant of pixel-blocking dust particles on the face of the sensor. Their effect is simply integrated out by the TDI sensor.

a. Focussed quasi-Lambertian illumination.

A disadvantage of most forms of diffuse illumination, and in particular of most imaginable realizations of quasi-Lambertian illumination, is that they are very wasteful of light.

In the design of a high-speed optical inspection machine, system performance is often limited by the amount of available light. If quasi-Lambertian illumination is achieved at the expense of great waste of light, it may be necessary to slow the machine down in order to maintain an adequate signal to noise ratio.

The essential feature of the present invention is that it provides focussing elements, in at least one axis, so as to achieve quasi-Lambertian illumination within the limited ares that is to be viewed by a sensor, while minimizing the wastage of light to illuminate non-viewed areas.

It will also be seen below that the inclusion of an illumination-controlling slit to limit the quasi-Lambertian illumination further improves the signal-to-noise ratio by suppressing noise as well as by enhancing signal. This is a second advantage of the present invention.

It will further appear below that the particular embodiments of our invention that are designed to work with generally-linear detector arrays achieve efficient focussed high-NA illumination over a very long field of view.

While the basic invention is the provision of focussed quasi-Lambertian illumination, there are additional design principles that should be incorporated in the design to optimize the usefulness of the inspection system of the present invention. In the design of optical illuminator 20 of the present invention the viewing lens has an NA of 0.06, and the illumination NA is approximately 0.9.

It is well known that, in conformance with the second law of thermodynamics, no illumination optical system can achieve an apparent brightness greater than that of the light emitting source. In practical terms, this means that if the light source used in a certain system has a surface area of ten square inches, then the most efficient possible design of illumination optics will deliver all of the emitted light to an area of ten square inches, and most illuminators actually achievable will spread the light over a larger area than ten square inches. It may therefore be concluded that, for maximal efficiency in design of a quasi-Lambertian illuminator, the light source must be of dimension comparable to or smaller than the area to be illuminated.

A second requirement, in the design of an efficient quasi-Lambertian illuminator, is that focussing means must be provided, in at least one axis, so that light rays which naturally diverge from the source will be reconverged toward the object being illuminated.

A third requirement is that the combination of whatever focussing and non-focussing optical elements are provided in the illuminator should ensure that the sky above the object appears substantially uniform from all angles above the object, and not just in one cross-section. An example of the application of this principle will appear in the discussion below of the particular incandescent-lamp implementation of a focussed quasi-Lambertian illuminator.

Figure 6:
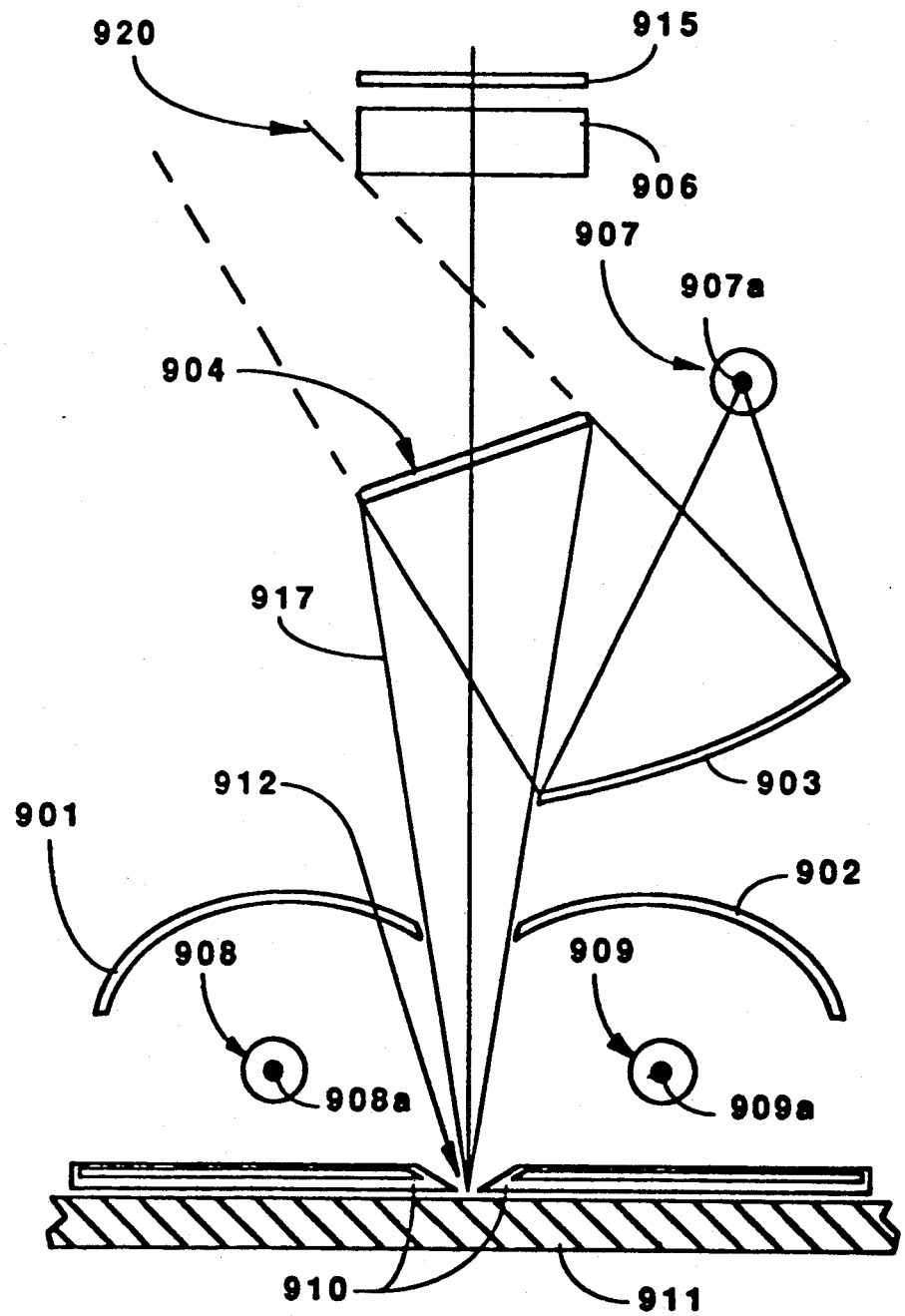
FIG. 6 is a cross-sectional schematic representation of a quasi-Lambertian reflected light illuminator of the present invention.

In the illuminator of the present invention, the focussing optical elements are elliptical cylinders which provide convergence in only one plane (see mirrors 901, 902, and 903, in FIG. 6). Flat end mirrors 1102 and 1103 (FIG. 7) are perpendicular to the lamp filaments (907a, 908a, and 909a) and to the axes of the elliptical cylinders of mirrors 901, 902 and 903; these end mirrors provide multiple reflections of the ellipses and lamps creating the equivalent of very long lamps and elliptical reflectors when viewed from the pwb target. Thus the combination of end mirrors (1102 and 1103 and cylindrical focussing mirrors (901, 902 and 903) has the effect of causing the object to see a uniform sky in all directions.

In the design of the focussed quasi-Lambertian illuminator for inspection of surfaces, a design principle is to trace rays from the workpiece back toward the filament that emits the illumination. Taking into account the tolerances of system manufacture, it should be ensured that every such ray eventually strikes the region occupied by the filament, and that the net loss incurred by the ray due to surface reflections should not exceed 20%, and preferably should not exceed 10%.

What is unexpected in the illuminator of the present invention is that it achieves efficient focussed high-NA illumination over a very large linear field, by providing efficient optical coupling to a generally-linear light source. It is also unexpected that the present invention illuminator provides substantially-uniform high-NA illumination in both axes, said illumination being focussed in at least one axis, without requiring the illumination to pass through the same lens that is used to form an image on an image sensor. This achievement optimizes the design to reduce the cost of the sensor lens.

b. Removable slit to improve signal to noise ratio

When illumination of very high numerical apertures is used to inspect pwb's, a surprising phenomenon occurs, which must be overcome if high-angle illumination is to be used. This phenomenon is illustrated by FIGS. 8 and 9.

Figures 8, 9:
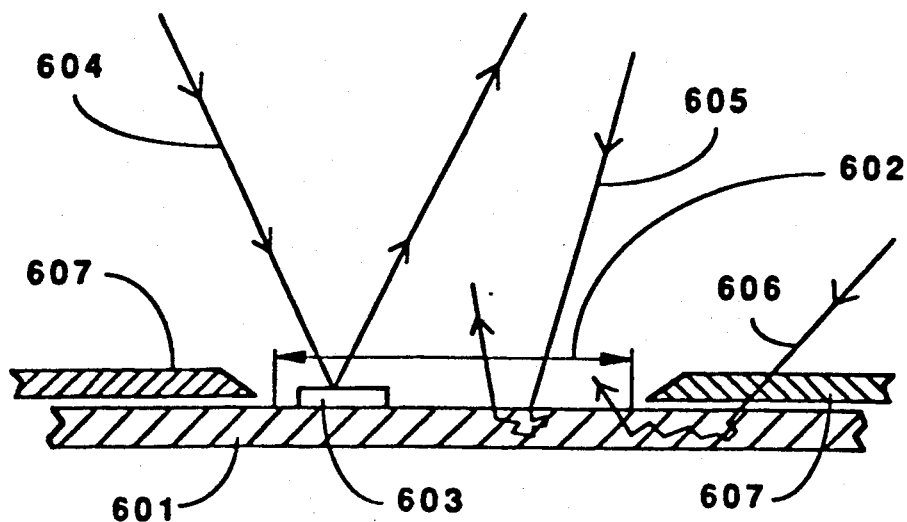
FIG. 8 is a cross-sectional view of a pwb to illustrate the effect of incident and reflected light rays when the pwb is illuminated through a low and a high N.A., with and without the use of an illumination-restricting slit.
FIG. 9 is a set of histograms that illustrate the contrast of the illuminated fiberglass substrate and the copper conductor for three different conditions of N.A. and the presence of a slit in the configuration of FIG. 8.

Begin by imaging FIG. 8 with slit assembly 607 absent. A focussed quasi-Lambertian illumination system provides rays of light at many angles. The illumination strikes region 602 which is viewed by the optical sensor, and also, because of imperfections in the illuminator, strikes areas outside region 602. The excess illumination area is made as small as possible in order to conserve light, but it is impossible to force all the light to strike within region 602.

Light rays 604, 605, and 606 are selected examples of the many rays which are present in the system. Ray 604 is shown striking a portion of conductor 603 and reflecting at such an angle that it strikes the fiberglass substrate, diffuses randomly through the substrate material, and emerges at a point within viewed region 602, where it will contribute to the apparent brightness of the substrate at the emergence point. Ray 606 strikes the substrate at a point outside the viewed region 602, and diffused into the viewed region before it emerges, so that ray 606 also contributes to the apparent brightness of the substrate in the viewed region 602.

The usual mode of viewing a pattern of copper conductors on a fiberglass substrate is to rely on the fact that the apparent brightness of copper exceeds the apparent brightness of the fiberglass substrate. Consider now the effect on copper/fiberglass contrast of increasing the numerical aperture of illumination. When the NA is low, certain regions of the copper, which happen to be nearly level, will appear to be bright. Regions which are tilted away from level will appear dark. Thus the histogram of copper reflectivity, as seen in FIG. 9, condition 1, will be broad.

Under this same low-NA illumination condition, a large fraction of the light rays entering the fiberglass substrate will emerge at angles such that they escape from the optical system. A random sample of these rays, after diffusion, will emerge in such a position and at such an angle that they can be seen. Because of the multiple refractions undergone by every light ray as it travels in the substrate, light intensities will be thoroughly randomized, and the general brightness of the substrate will seem rather uniform. Because at least half the diffusion rays randomly pass toward the back side of the substrate rather than the viewed side, and because some of the rays are absorbed without every emerging from the substrate material, the substrate generally appears to be darker than the copper. The uniformity and darkness of the substrate appear in FIG. 9 condition 1 as the narrowness and small average brightness value of the histogram peak corresponding to the substrate material.

Now consider how the situation changes as the numerical aperture of the illumination system is increased. The copper areas which were initially bright do not greatly change in brightness, because the added high-angle rays, when they strike these nearly-level areas, are reflected out of the optical system. Copper areas which were initially dark will tend to increase in brightness, as has been previously explained. The net effect is to reduce mottling, but not greatly to increase the level of the peak brightness seen from copper areas. The effect on the Condition 2 histogram is that the copper peak gets narrower, but not much further to the right on the brightness axis.

The effect on the diffusive substrate material is different. Because of the diffusive action of the substrate, any ray that enters the material has an approximately constant change of emerging at such an angle as to be seen by the optical system. As the range of provided illumination angles is increased, the total amount of light entering the substrate is increased, and the observed brightness increases in proportion. This situation is exacerbated by rays such as ray 606, which strike the substrate outside the viewing area, so that they can contribute nothing to the apparent brightness of conductors, but because of diffusion, they can increase the undesirable apparent brightness of the substrate.

The net effect of increasing greatly the numerical aperture of illumination is a histogram such as that shown in FIG. 9, condition 2, where the substrate peak overlaps the copper peak. The brightness points on the substrate, in other words, look brighter than the dimmest points on the copper. The computer can no longer distinguish unambiguously between copper and substrate. We have narrowed the copper peak in the histogram, which is desirable, but have introduced another highly-undesirable effect.

A solution to this phenomenon is the addition of means to restrict the illumination to a narrow region on the substrate, thereby eliminating rays such as ray 606, which have only undesirable effects. The slit assembly 607 shown in FIG. 8 is one such means. In one experiment with 0.9 NA illumination, it was found that by changing from a 1.6 mm slit to a 0.8 mm slit, there was a change from an unacceptable Condition 2 histogram, to a desirable histogram such as that in FIG. 9, condition 3.

c. White Light Source, with spectral selection filter

In designing an optical inspection machine for pwbs, it is desirable to be able to vary the color of light seen by the sensor, in order to optimize contrast in particular inspection applications. For example, it is sometimes desirable to inspect patterned photoresist on copper, prior to the etching of the copper. If defects are found in the photoresist pattern, the resist can be stripped and replaced, without wasting the substrate. Photoresist is supplied in several colors, and successful inspection requires selection of inspection light wavelengths that will optimize contrast between the resist and the copper.

Figure 10:
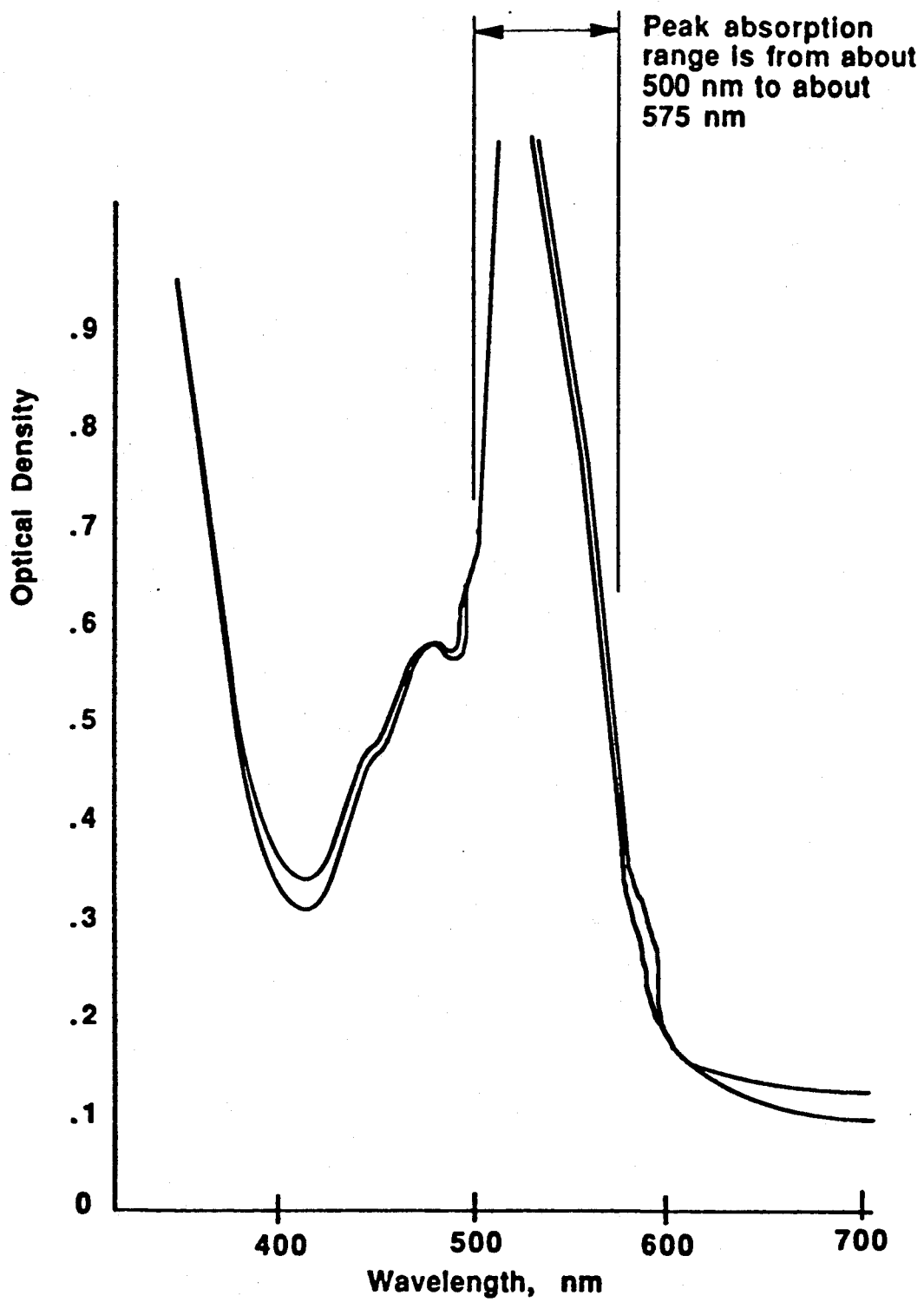
FIG. 10 is a graph of the transmission spectrum of DuPont Riston 216R photoresist.

For example, FIG. 10 shows the transmission spectrum of Dupont Riston (TM) 215R, a commercially available red photoresist material. By restricting the inspection wavelengths to a range between 500 and 575 nm, we can make the resist appear to be dark, while the copper will be bright; the reflectivity of copper varies from about 63% at 500 nm to about 80% at 575 nm.

In order for an optical inspection machine to exhibit maximum flexibility in the inspection of pwbs, the following items are suggested:

a. Interchangeable color filter (915, FIG. 6), permitting selection of different filters to optimize the inspection of different materials.
b. A light source which has available substantial energy throughout a wide spectral region, such as 500 to 700 nm.
c. An image sensor which is responsive throughout the entire useful spectral band of the light source.
d. Auxiliary enhancing means for improving signal to noise ratio, that enable the machine to run at high speed despite the loss of signal level entailed in use of a narrow-band filter, for example, a TDI sensor, a light source whose physical size is similar to the size of the region viewed by our photosensor, and a focussed-light illuminator. These features jointly suffice to permit 100 Mpixel/sec. operation even with a filter installed that permits only 500 to 575 nm radiation to reach the sensor.

It is not new to provide a filtered light source. For example, the Optrotech Vision 105 provides interchangeable filters. Comparing the machine of the present invention to that one, however, we see that Optrotech has needed to employ a high-efficiency sodium arc lamp in order to get enough light to keep their machine working even at 10 Mpixel/s. This lamp does not provide substantial radiation in the wavelength range below about 550 nm. The present invention is able to use less efficient lamps (tungsten-halogen), which do provide a useful amount of energy to 500 nm, because of the provision of various above-cited techniques that enhance the efficiency with which available light is used. What is new is the combination of a filtered broadband light source with the efficiency-enhanced features that make such a light source usable for high-speed inspection.

The use of a 64 row TDI sensor with an efficiency of 64 times that of a normal sensor is what allows the use of tungsten-halogen lamps (907, 908 and 909 FIG. 6).

d. Implementations with multiple linear tungsten-filament lamps.

Figure 7:
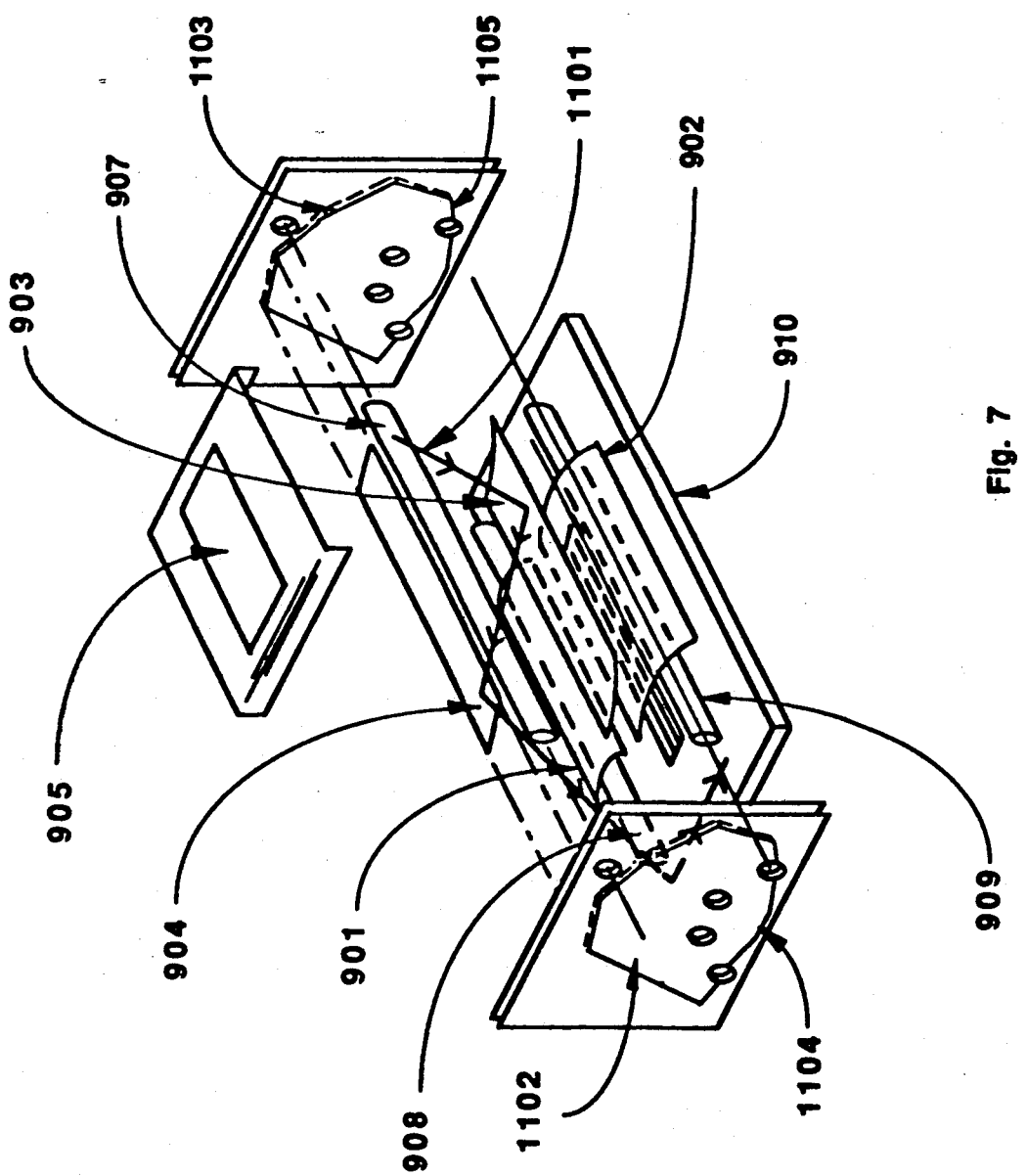
FIG. 7 is a perspective view of the illuminator of FIG. 6.
Figure 11:
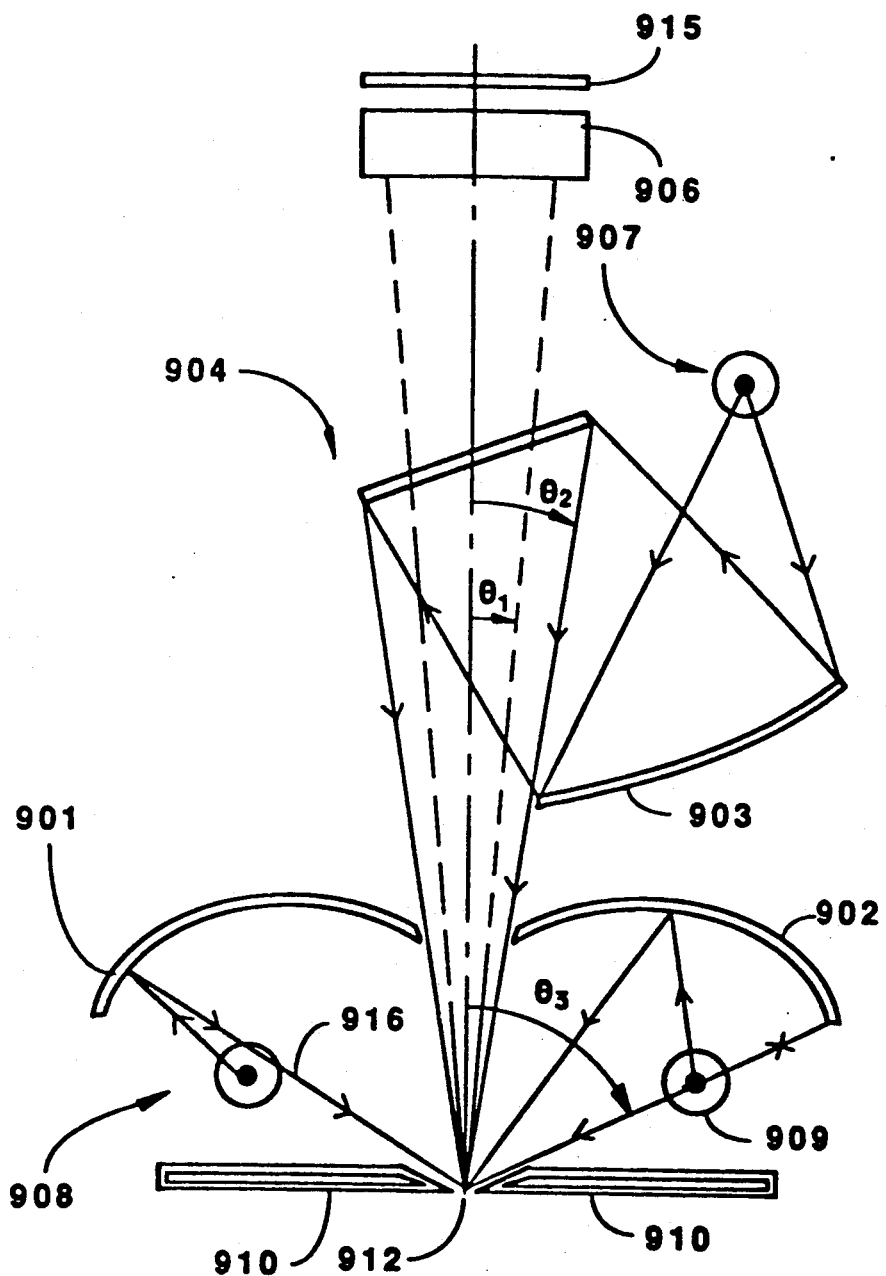
FIG. 11 is the same basic figure as that of FIG. 6 wherein the reflection of selected light rays is illustrated.

FIGS. 6, 7 and 11 show one embodiment of the design of the present invention. The light sources in this illuminator are three linear-filament tungsten-halogen lamps 907, 908 and 909. Each lamp has a filament (907a, 908a and 909a respectively, located approximately centrally in a tubular glass envelope). Each lamp filament is imaged in the inspection area 912. Filament 908a is imaged by elliptical mirror 901, filament 909a by elliptical mirror 902, and filament 907a by the combination of elliptical mirror 903 and beamsplitter 904.

The filament of lamp 909 lies at the first focus of elliptical reflector 909 and the linear illuminated area 912 lies at the second focus of the same ellipse. Thus, due to the well-known imaging properties of an ellipse, light emanating, from filament 909 that strikes reflector 902 is focussed in a line along area 912. The imaging of filament 910 by reflector 901 corresponds exactly to the imaging of filament 909 by reflector 902. Similarly filament 907 lies at the first focus of the upper elliptical reflector 903 and area 912 lies at the second focus of reflector 903 as reflected from beamsplitter 904.

Any generally-linear light source may be used with the described optical system. One alternative is to use capillary arc gas discharge lamps.

The inspection area 912 is viewed, through beamsplitter 904, by lens 906, whose function is to form the image of area 912 on a photo sensor (not shown) through sensor lens system 906. For best efficiency, the sensor will be of the TDI type as discussed below. Slit assembly 910 is provided, as has been explained above, to improve the contrast between copper and fiberglass material. End mirrors 1102 and 1103 (visible in the exploded view of FIG. 7) are so positioned as to make the lamp filaments appear to be of infinite extent. Because of these mirrors, skew rays (such as ray 1101 in FIG. 7) find their way to observation region 912 by undergoing one or more reflection from the end mirrors enroute to region 912.

The presence of the end mirrors 1102 and 1103 is responsible for the fact that this illuminator delivers substantially uniform illumination not only in the cross-sectional plane of FIGS. 6 and 11, but also in the perpendicular plane and all intermediate planes. This is necessary if we are to have effective quasi-Lambertian illumination. An imaginary observer stationed on the observation region 912 and looking up into the sky, would see the surface of a lamp filament in any direction he looked, out to an angle of $\theta_3$ from the surface normal. FIG. 11 shows that limiting angle $\theta_3$ is established by the edges of mirrors 901 and 902 in the plane of FIG. 11. FIG. 7 shows that limiting angle $\theta_3$ is established in the orthogonal plane by the lower edges 1104 and 1105 of end mirrors 1102 and 1103.

The relationship between angles $\theta_1$ and $\theta_2$ is also important. $\theta_1$ is the angle from the surface normal within which sensor lens 906 collects light. This angle will typically range up to about 5.74 degrees (0.1 NA), or perhaps somewhat larger. Angle $\theta_2$ is from the normal to the inner edge of mirrors 902 and 901. $\Theta_2$ is greater than $\theta_1$, so that the inner mirror edges do not obstruct the light rays travelling from the observation region 912 to the viewing lens 906 Angle. $\theta_3$ from the surface normal to the outside edges of the mirrors, establishes the extent to which the illuminator approximates a full uniform sky. In the current design, this angle is approximately 70°, which corresponds to a numerical aperture of 0.94.

Illumination rays such as ray 916. (FIG. 11) which are reflected so as to pass through the lam envelope on their way from the mirror to the observation area, may be somewhat deflected by the envelope, and their intensity will be somewhat reduced because of the partial reflections that occur at each glass/air interface. It is therefore a feature of the preferred embodiment of the invention that the lamp filaments are positioned at an azimuth close to extreme illumination angle $\theta_3$. Thus the distorting and intensity reducing effects of the glass envelope are concentrated in the extreme-angle rays. Experience has shown that these rays are less important in reducing apparent mottling of rough surfaces than are rays that strike the object closer to normal incidence.

The focussing action of the elliptical mirrors causes this system to be much more efficient than an illuminator not having focussing. Putting aside the losses caused by imperfect mirror and beamsplitter reflectivity, and illumination imperfections caused by non-straight lamp filaments, the brightness experienced by our imaginary observer is the same as if the entire sky above him were filled with white-hot tungsten, at a color temperature which may exceed 3100° K.

The arrangement of three uniaxially-focussing mirrors and a beamsplitter, in combination with generally linear light sources and end mirrors which make those light sources appear to be of infinite extent, is believed to be innovative.

It is also believed to be innovative to have an arrangement of uniaxially focussing illuminators and linear light sources, in which the sky is divided into two portions as follows: there is an outer portion of the sky in which the mirrors may be fully reflective, and an inner portion in which at least one partially-transmissive object, such as beamsplitter 904, is required in order for a viewing lens to view the object through the illuminator.

There is a temperature to use the nomenclature of microscope illuminators, to describe the illuminator of the present invention as comprising a "brightfield" portion, which provides rays generally within an inner viewing cone. This is not strictly correct, as may be seen in FIG. 7. In the direction along the long axis of line-like observation region 921, the upper lamp and mirror system provide both rays at angles inside viewing cone 917, and other rays that lie far outside cone 917. Thus the upper illuminator 907 shares come brightfield and some darkfield characteristics.

Figure 12:
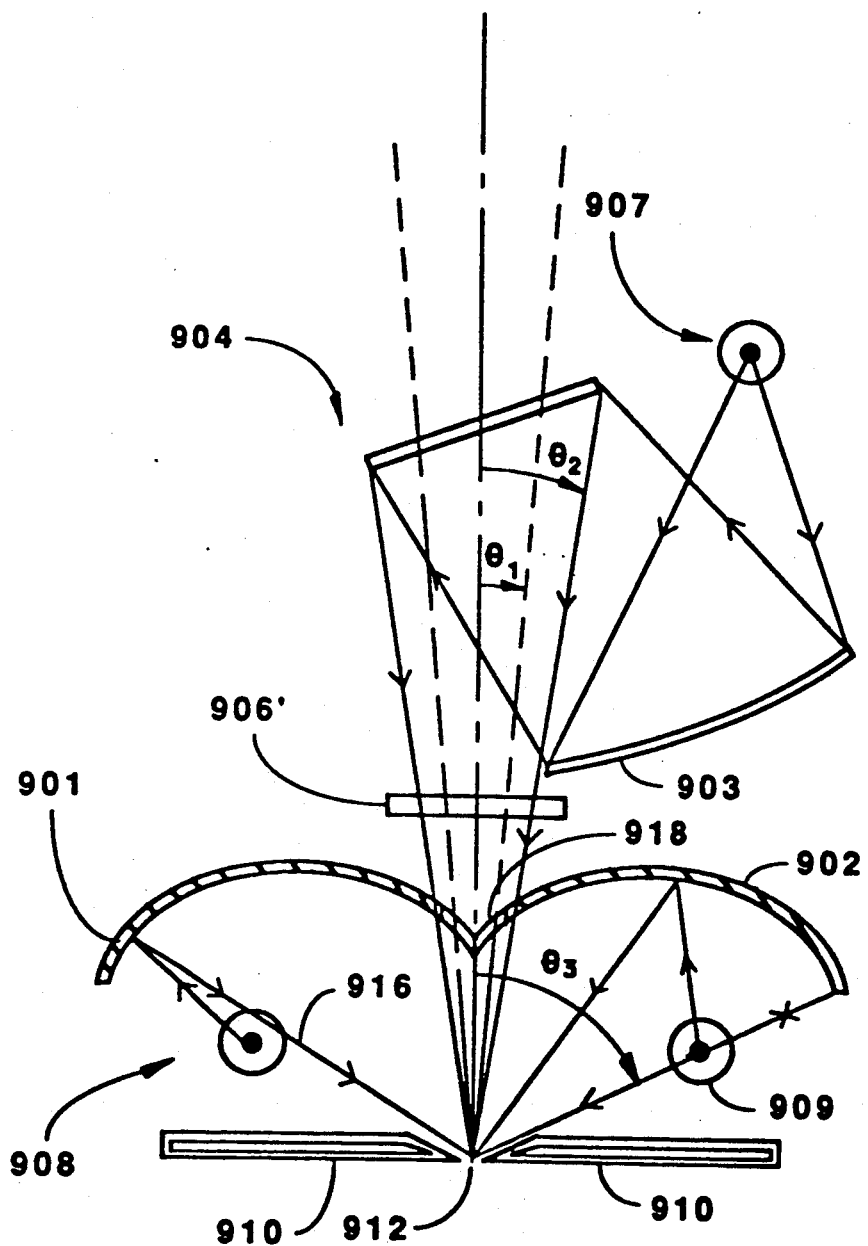
FIG. 12 is a modified arrangement from that of FIG. 6 for the true combination of brightfield and darkfield illumination.

A variation of the design of the present invention that is useful in some circumstances is an arrangement in which the sky is in fact partitioned into true brightfield and darkfield sections. To do this (FIG. 12) the beam splitter 904 is placed above lens 906', so as to provide brightfield illumination through the lens. Mirrors 901' and 902' extend and intersect in the middle, with an open circular region 918 of angular extent $\theta_1$, so that they provide wideangle darkfield illumination, in all regions not illuminated by lens 906'.

An advantage of the optical arrangement of FIG. 6 in which the beamsplitter 904 is below the sensor lens 906, is that there is no opportunity for stray light to be reflected from the lens back into the sensor. Because of the very high levels of illumination used in high-speed inspection systems, suppression of such stray light is important.

It is desirable for the reflective surfaces in the illuminator to have wavelength-dependent properties. Each tungsten lamp filament emits a wide range of wavelengths, primarily in the visible and infrared, but only a selected portion of the spectrum, typically in the 500 to 700 nm range, is useful. To the extent that other wavelengths are reflected, and focussed on the observation region 912, they will contribute to undesired heating of the pwb.

One approach to wavelength selection is to make the mirrors of glass, and to make the mirror coatings multilayer dielectric cold mirrors, which are designed to reflect the wavelengths of interest, and to transmit other wavelengths. Another approach, suitable if the mirror substrates are of opaque material such as electroformed nickels, is to employ a dark mirror coating. Dark mirror coatings are also multilayer coatings, designed to reflect selected wavelengths and efficiently couple others into the substrate material, where they are absorbed.

Figure 13:
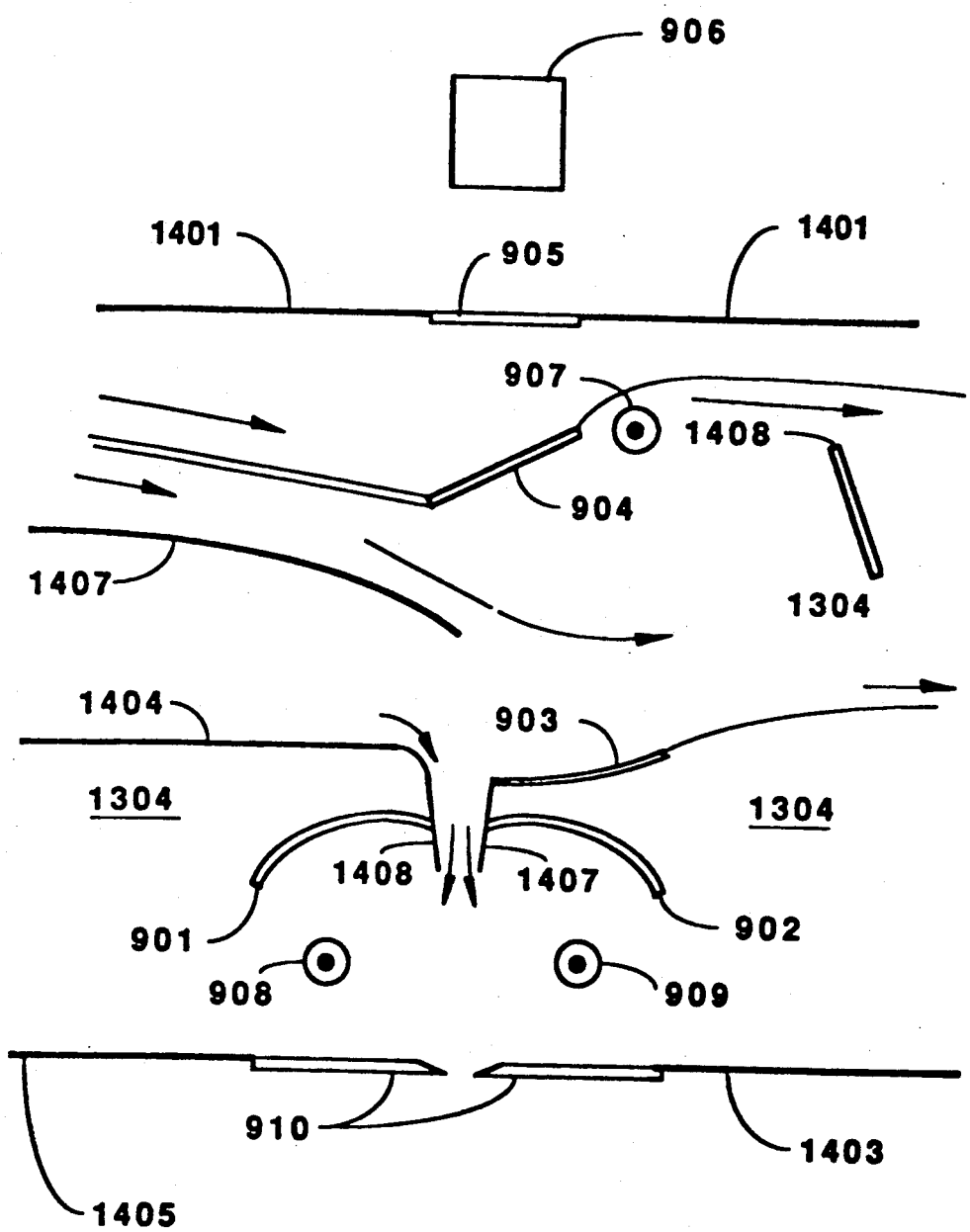
FIG. 13 is a cross-sectional view of the illuminator of FIG. 6 showing an air flow control system for cooling the lamps and mirrors, and, therefore minimizing Schlieren effects.

In either case, it is necessary to ensure that the non-reflected energy is effectively carried away in a cooling airstream (see FIG. 13). In the case of dark mirrors, the unwanted energy serves to heat the mirror substrates. Air flowing directly over the substrates will then absorb the heat and carry it away.

In order to minimize the amount of waste energy which must be transferred to the cooling air stream, it may be desirable to provide the tubular envelopes of the lamps with dielectric coatings, so designed as to transmit desired visible wavelengths and reflect at least a portion of the unwanted longwave radiation back onto the filament. Such lamps are available, for example, from General Electric, under the tradename "Watt-miser".

It may also be desireable to provide auxiliary tubes, surrounding the lamp envelope, the infrared-rejected coating being provided on the auxiliary tube. This approach has the advantage of allowing lower-cost uncoated lamps to be used. The relatively expensive lamp coating would reside on the auxiliary tubes, which do not require periodic replacement.

Because beamsplitter 904 is partially transmissive, a beam of waste energy is transmitted through the beamsplitter. Ray 920, in FIG. 6, is the extreme uppermost ray of this beam. An important design feature is that sensor lens 906 is placed high enough so that the waste energy beam does not enter the lens housing. If the beam 920 did enter, it would be likely to bounce around inside the housing, giving rise to stray-light artifacts in the image.

An important feature of the illuminator design shown in FIGS. 6, 7 and 11 is that beamsplitter 904 is tilted at a relatively small angle to the optical axis. A more conventional way to configure a vertical illuminator would be with the beamsplitter at 45 degrees. In the system of the present invention, however, it is necessary for lens 906 of have a relatively high numerical aperture (up to NA 0.1), and to exhibit low optical aberrations. Furthermore, the low-aberration performance must be maintained over a substantial depth of focus, on the order of ±0.002 inches. It has been determined that a 1 mm thick beamsplitter tilted at 45° would contribute so much aberration in the viewing optical system as to make the required combination of resolution and depth of focus unattainable, even with a perfect lens.

A tilted glass plate contributes less aberration as the angle of tilt is reduced. It has therefore been found advantageous to make the angle as small as possible, consistent with other design constraints. This led to a choice of tilt of about 20°.

Even if the glass plate could be completely untilted, there would remain some spherical aberration, but this it not a serious problem, as it can be corrected by the proper design of the lens 906. The astigmatism resulting from tilting the plate cannot easily be corrected in the lens design (partial correction by means of tilted lens elements might be possible, but it would be expensive), so tilt must be minimized.

As will be discussed further below, it is advantageous to provide a flow of cooling air through the illuminator, to carry off heat generated by the lamps and to suppress Schlieren effects in the viewing optical path. Window 905 serves to confine the air flow and to keep dust off beamsplitter 904 while permitting lens 906 to see observation region 912.

An important feature of slit assembly 910 is that it is removable and that it floats on an integral air bearing above the surface being inspected, independent of the housing of the illuminator. In the inspection of some kinds of pwb's, such as multilayer boards with a large amount of warpage, the surface being inspected may move up and down over a distance greater than the optical depth of field as the board is scanned beneath the optical inspection head. The inspection machine contains a focussing mechanism that is designed to move the optical head up and down to follow the motion of the board.

Figure 15A:
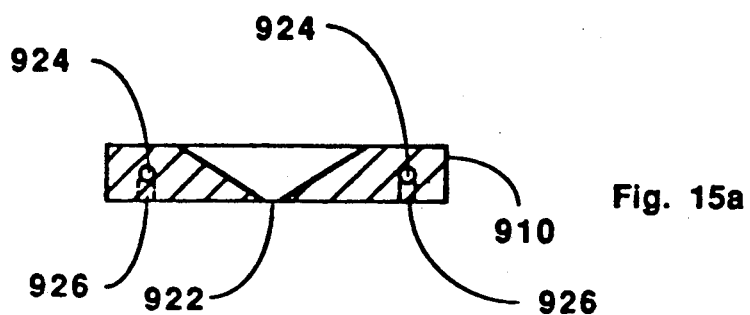
FIGS. 15a and 15b are plan vertical cross-sectional and bottom views, respectively of the slit assembly and integral air bearing of the illuminator of the present invention.
Figure 15B:
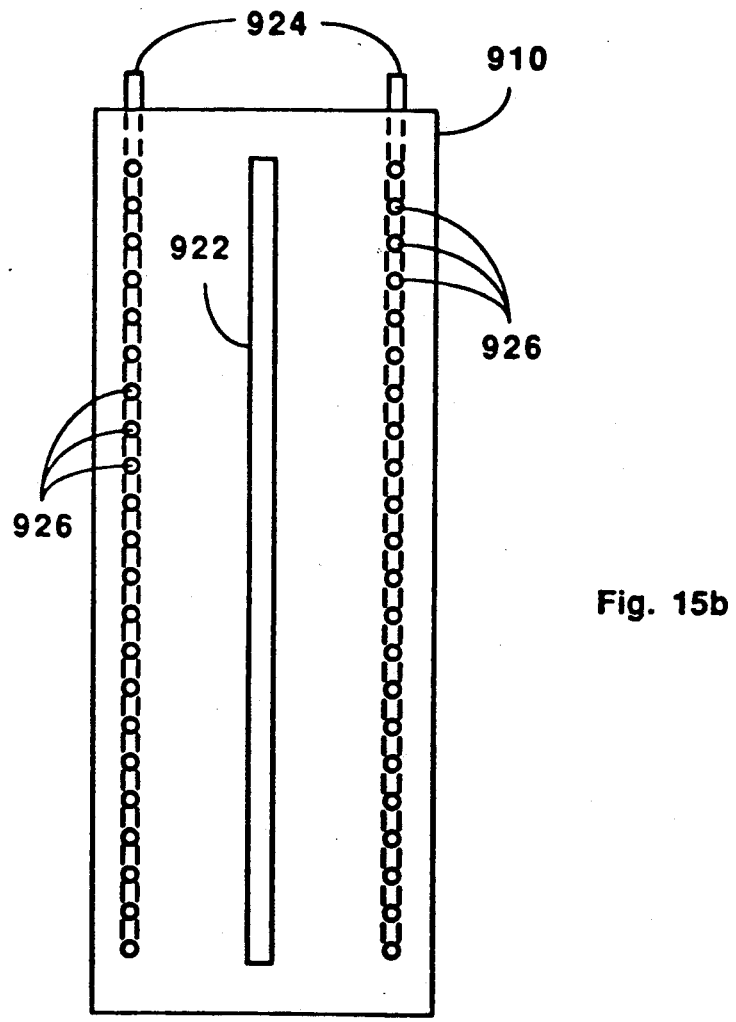

FIGS. 15a and 15b illustrate the slit assembly 910 of the present invention with its integral air bearing. Slit 922 runs the length of the assembly and when the assembly is installed beneath illuminator 20, slit 922 is substantially as long as the optical field of view parallel to the filament of lamps 907-910. Slit assembly 910 also defines, parallel to slit 922, air channels 924 which connect to a 60 psi air supply (not shown) to apply positive air flow thereto. Extending through the bottom surface of slit assembly 910 and connected to one of air channels 924 are selectively spaced air outlet orifices 926. Thus, as a result of the size, spacing and number of ducts 926, and the air pressure applied to channels 924, slit assembly 910 will float closely above the surface of the item 911 to be inspected. If the air pressure is maintained constant, then the spacing between the inspection surface 911 and the slit assembly 910 will remain substantially constant.

Figure 14:
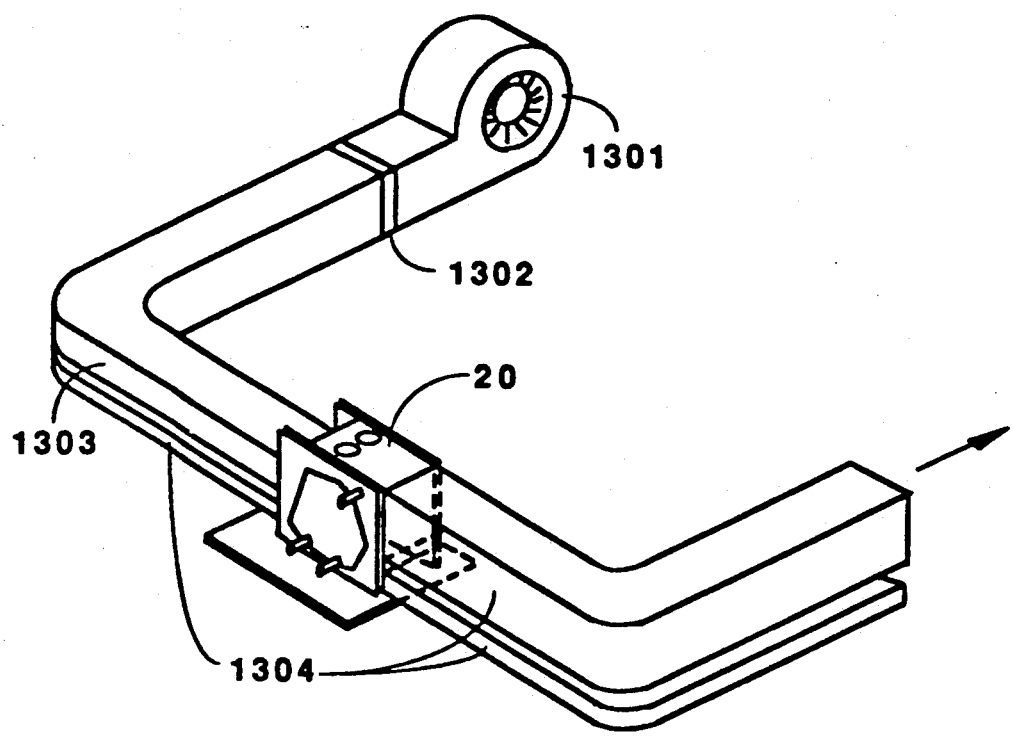
FIG. 14 is a perspective view of the illuminator cooling system and related ducts.

FIGS. 13 and 14 illustrate a suitable air flow system 22 for removing heat and Schlieren effects from the illuminator assembly 20. A typical illuminator 20 may dissipate on the order of 3 kilowatts of heat, which may require an air flow of approximately 300 cubic feet per minute (cfm) to remove the heat without an unacceptable temperature rise of the exhaust air. The cooling system 22 comprises blower 1301, air filter 1302, inlet air duct 1303, flow-directing baffles such as 1407 and exhaust ducts 1304.

Vanes 1407 serve to duct the air downward through the optical path. They lie just outside and parallel to the extreme rays from the object to the viewing lens 906. Note that they project slightly below the elliptical reflectors 901 and 902. An observer on the illuminated line would see only the edges of vanes 1407 and 1408, because the planes of these vanes lie along the lines of sight originating at the center of the field-of-view. This minimizes the amount of sky that is dark due to their presence. The air flow ducted by these vanes serves to sweep the hot turbulent air from the optical path to minimize thermal gradients along the path of the viewing optics and thus minimize Schlieren effects. (Schlieren effects are the refraction of light rays due to thermally induced variations in the index of refraction of the air through which the light passes.)

One feature of the design of the cooling system is that the airflow path is sufficiently airtight to avoid significant discharge of warm air inside the machine. The warm air is ducted outside the machine, so that it does not contribute to inaccuracies in the performance of the imaging optical system.

Another requirement in the design of the cooling system is that the lamp envelopes must not be overcooled. It is known that for long operating life of a tungsten-halogen lamp, the wall temperature of the lamp should not be allowed to fall below about 250° C. when the filament is at full operating temperature. If the wall does cool below this level, there occurs suppression of the chemical cycle that moves deposited tungsten from the lamp wall back to the filament. The results are that the lamp wall turns black and the filament tends to burn through.

The duct pattern shown in FIGS. 13 and 14 was empirically developed to meet this bulb temperature requirement, while simultaneously meeting the Schlieren suppression requirement.

An alternative arrangement for meeting the bulb temperature requirement is to surround the bulb envelope with an auxiliary glass tube, such as the infrared-reflecting auxiliary tube discussed above. The presence of this tube protects the lamp envelope from direct impact of air flow, so that air flow velocity can be made significantly higher without unduly lowering the temperature of the lamp envelope.

A system design feature necessary for the effective use of illuminator 20 is apparatus to balance the light intensity produced by each of the three lamps. In order to optimally suppress mottling effects on rough surfaces, all parts of the sky above the observation area should be of approximately uniform brightness. One way to achieve this brightness is to place a uniform diffusely-scattering sample in the observation region, operate the lamps one at a time, and adjust the lamp amplitudes so that the peak brightness seen in each case reaches a predetermined value.

e. Incoherent Fluorescent Illuminator.

This is a second embodiment of the present invention.

The discussion above has centered on the use of focussed quasi-Lambertian illumination to suppress surface mottling on rough-surfaced materials to be optically inspected. An alternative way to accomplish this end is to illuminate to pwb with short-wave radiation, for example in the range from 400 to 500 nm, and to view the longer-wave radiation which may result from fluorescence stimulated by the shortwave radiation.

Many types of pwb substrate material will fluoresce to some extent, while clean metallic conductor surfaces will not, so much a scheme produces high-contrast image in which the conductors appear black and the substrate material appears bright. Because the conductors are black, their surface mottling disappears. In some cases, it is practical to enhance greatly the fluorescence efficiency of the substrate, thus improving the signal-to-noise ratio, by adding a fluorescent dye to the substrate.

Optical inspection systems utilizing this principle are known. Lincoln Laser Corporation sells a fluorescence-based pwb inspection machine in which the stimulating ration is provided by a scanning 442 nm beam from a helium-cadmium laser. Such a machine has been described in U.S. Pat. No. 4,556,903, issued Dec. 3, 1985 to Frank H. Blitchington and David B. Haught.

The use of a laser to stimulate fluorescence has several disadvantages, which could be overcome if it were possible to use incoherent illumination as the stimulant. Among the advantages of incoherent illumination are:
a. Incoherent light sources are less expensive, especially when compared on the basis of cost per watt of delivered light, than are laser sources.
b. Imaging systems based on incoherent illumination and solid state detector arrays can more economically be made to have high accuracy in locating features than can a laser scanner, because of all the sources of inaccuracy associated with the moving parts, such as rotating polygonal mirrors, that are commonly used in laser scanners.
c. It is easier to achieve wavelength flexibility in an incoherent illuminator, than in a laser illuminator. This is desirable because different materials will respond optimally to different stimulating wavelengths.

The difficulty in applying incoherent illumination to fluorescent pwb inspection has been that there has seemed to be too little light available for high-speed inspection. The laser-based systems have the advantage that all of the relatively weak light output of the laser (about 10 mW) can be concentrated on a very small spot (as small as a fraction of the fluorescent light emitted by that spot that can be collected by large-aperture detector optics. Light from a high-pressure short arc lamp (the brightest readily available incoherent light source) cannot in principle be concentrated on an area smaller than the surface area of the arc (practical systems, in fact, can only concentrate light on much larger areas than that of the arc surface), and the aperture of the imaging lens collecting the fluorescent light must typically be small enough that 1% or less of the fluorescent radiation will be delivered to the sensor array.

The applicants have recognized that the potential advantages of the incoherent fluorescence system can be realized, by combining an incoherent fluorescent source with one or more of a group of efficiency-enhancing devices.

The first such device is a Time-Delay Integration sensor (TDI sensor), whose application to automatic optical inspection is discussed below. One way to think of the benefit of the TDI sensor is to recognize that it effectively collects light from an area many times the width of the resolvable pixels (at least 64 pixel widths). Thus, if all the light from a fluorescence-stimulating source can be concentrated in an area 64 times the width of a pixel, the effect will be as good as if all that light were concentrated in one pixel width for a conventional linear array sensor. This does a lot to overcome the difficulty of focussing incoherent light on a small area.

Another efficiency-enhancing means is a concentrated-illumination system, such as that described above.

Figure 16A:
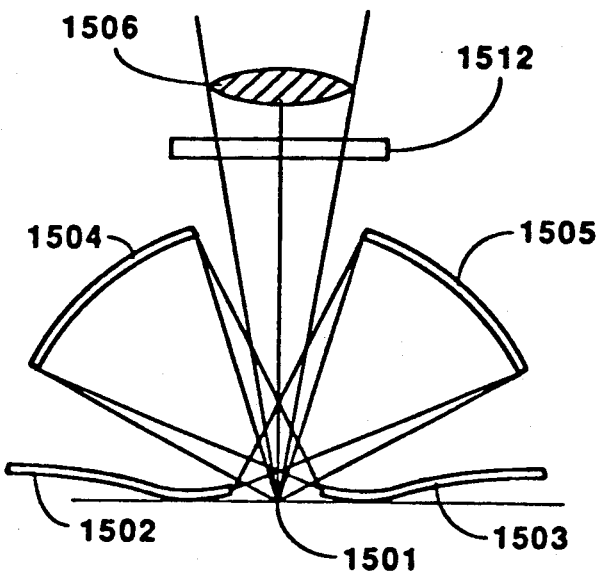
FIGS. 16a and 16b are plan cross-sectional and perspective views of a first embodiment of a fluorescence illuminator of the present invention.
Figure 16B:
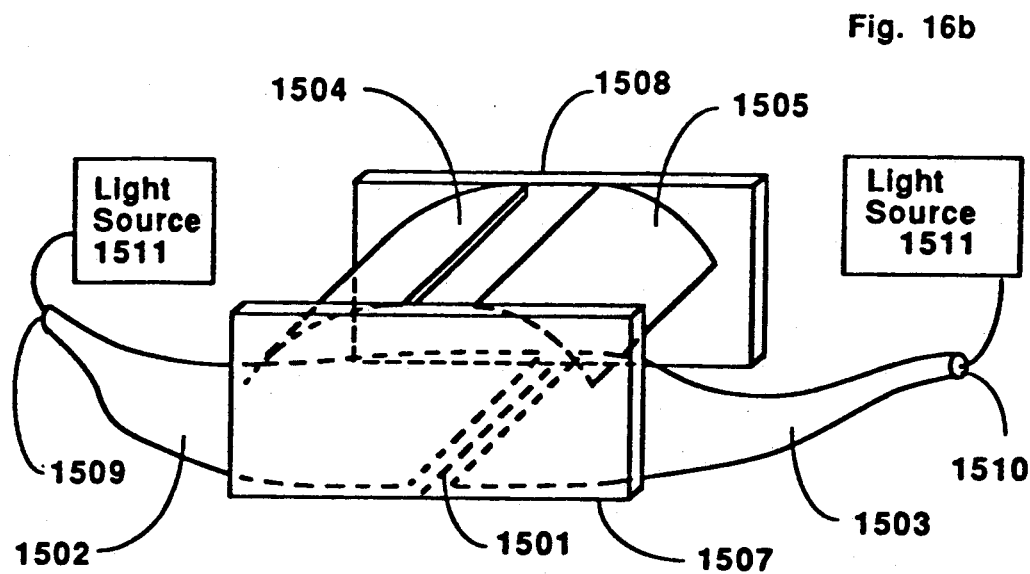

FIGS. 16a and 16b illustrate a first embodiment of a fluorescence illuminator made in accordance with the present invention. This embodiment incorporates a concentrated-illumination system adapted for use with a substantially-linear viewing region, and may also incorporate a TDI sensor. FIG. 16a is a medial cross-section and FIG. 16b is a perspective view of the illuminator.

Region 1501 is the line to be illuminated on the object to be inspected. If a TDI sensor is being used, this region will be on the order of 2000 pixels long and 64 pixels wide, where a pixel may be 0.001 inches or less, depending on the resolution which is desired. Short-wavelength light is brought into the illuminator by fiber optic bundles 1502 and 1503, whose exit ends are narrow in the view seen in FIG. 16a (e.g. about 0.005 inches in height), and as wide as the viewing line 1501 in the direction perpendicular to the section of FIG. 16a.

Mirror 1504 is a section of an elliptical cylinder, with foci at line 1501 and at the exit end of fiber bundle 1503. Mirror 1504 may be approximated by a section of a circular cylinder, approximating closely to the specified ellipse. Similarly, mirror 1505 is a section of an elliptical cylinder having foci on the exit end of bundle 1502 and line 1501, and this mirror also may be a segment of a circular cylinder approximating the optimal ellipse.

Lens 1506 is the viewing lens, which focuses a fluorescent-light image of line 1501 on the sensor (not shown). This sensor may be an ordinary solid-state linear diode array sensor, or it may be a TDI sensor.

Filter 1512 is a filter that blocks any short wavelength light from source 1511 that may be scattered off the substrate directly into the lens 1506, and passes the visible light resulting from fluorescence of the substrate.

As shown in FIG. 16b, the fiber optic bundles 1502 and 1503 are reshaped along their lengths, so that their entrance ends 1509 and 1510 are approximately circular. This makes it convenient to illuminate the entrance ends of the fibers efficiently with light gathered from a short-wave light source, such as 365 nm radiation from a high-pressure mercury arc. Because the details of construction of efficient illuminators to produce circular spots of light are well known, this part of the system has not been illustrated in detail, but is represented as block 1511.

It is important in the design of this system that a very large fraction of the light leaving the exit ends of the fiber bundles 1502 and 1503 to be delivered to the region that will be imaged on the detector. A first requirement, if this goal is to be achieved, is that the length of the arc of mirrors 1504 and 1505 be well-matched to the divergence angle of rays leaving the fiber bundles (see FIG. 16A), so that substantially all of the rays leaving the bundles are captured by these mirrors and converged toward line 1501. Since the divergence angle of rays leaving the fiber bundles will be substantially equal to the convergence angles of the entering rays, this requirement is met by proper matching of the optical design of light source 1511 to the angular extent of mirrors 1504 and 1505.

A second requirement in the design of the fluorescence illuminators of FIGS. 16a and 16b is that the width of the illuminated line 1501 not be substantially larger than the region viewed by the detector. This, in turn, requires that the height of the exit end of fiber optic bundles 1502 and 1503 be significantly smaller than the width of region 1501. This in turn implies a restriction on the diameter of entrance ends 1509 and 1510 of the fiber bundles.

Now it is well known that an efficiently designed light source will be characterized by a certain entendue, which is the product of the area of the region illuminated and the square of the numerical aperture of the converging illumination beam. If all the available light from a fiber arc lamp illuminator is to be collected, the designer has the freedom to illuminate a larger fiber bundle at a small NA or a smaller bundle at a large NA, but he may not arbitrarily choose both area and NA. Since the width of region 1501 has implied a specification of the area to be illuminated, the NA of the light entering the fiber bundles is determined. Because light will diverge at the same angle when it leaves the fiber bundles, this implies a requirement on the angular extent of mirror arcs 1504 and 1505. These arcs must be long enough so that, even with the restriction on the exit heights of bundles 1502 and 1503, substantially all of the light delivered by source 1511 can be delivered to region 1501.

It will usually be true that light emerging from the end of each optical fiber constituting bundles 1502 and 1503 will diverge approximately conically. If the bundles are made approximately the same width as the length of the line to be illuminated, which is desirable for efficiency and uniformity of illumination, then the fibers near the ends of region 1501 will radiate a significant portion of their output in directions that would carry the rays focussed by mirrors 1504 and 1505 into areas beyond region 1501. For this reason, we provide end mirrors 1507 and 108, to redirect such rays back toward region 1501. It will be clear to those skilled in optical design that the effect of mirrors 1507 and 1508 is to capture substantially all radiation originating from bundles 1502 and 1503 and direct it toward region 1501 where it will be useful.

Figure 17:
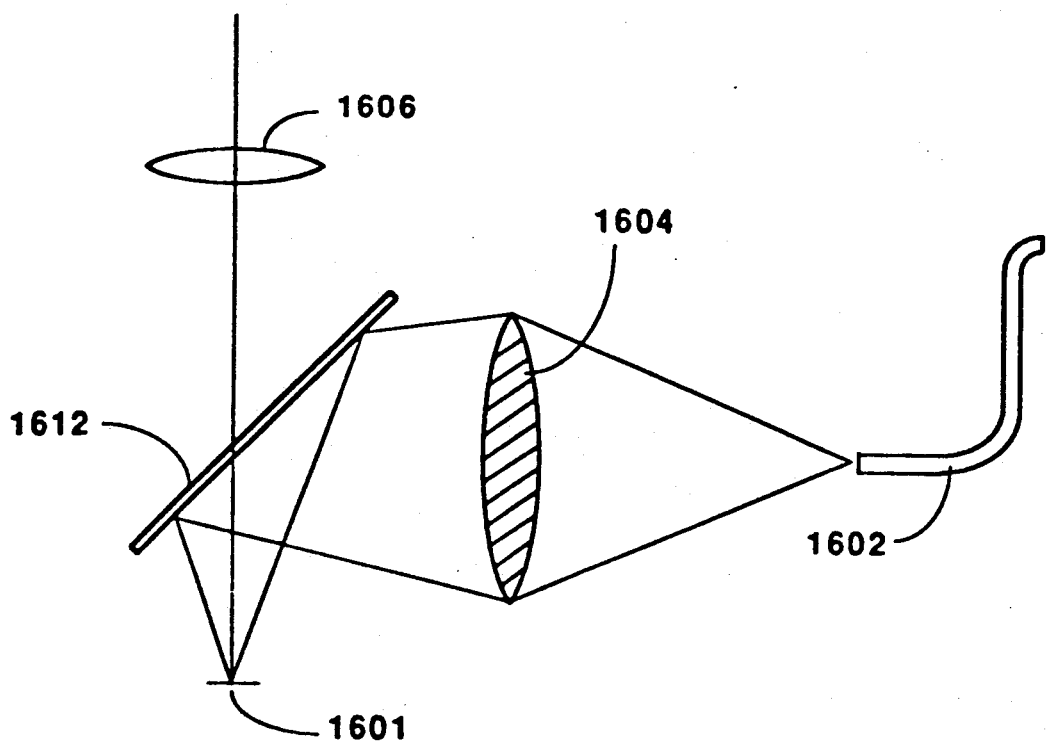
FIG. 17a is a schematic representation of a second embodiment of a fluorescence illuminator of the present invention.
FIG. 17b is a cross-sectional schematic representation of a illuminator capable of both reflected light and fluorescence illumination.
Figure 17:
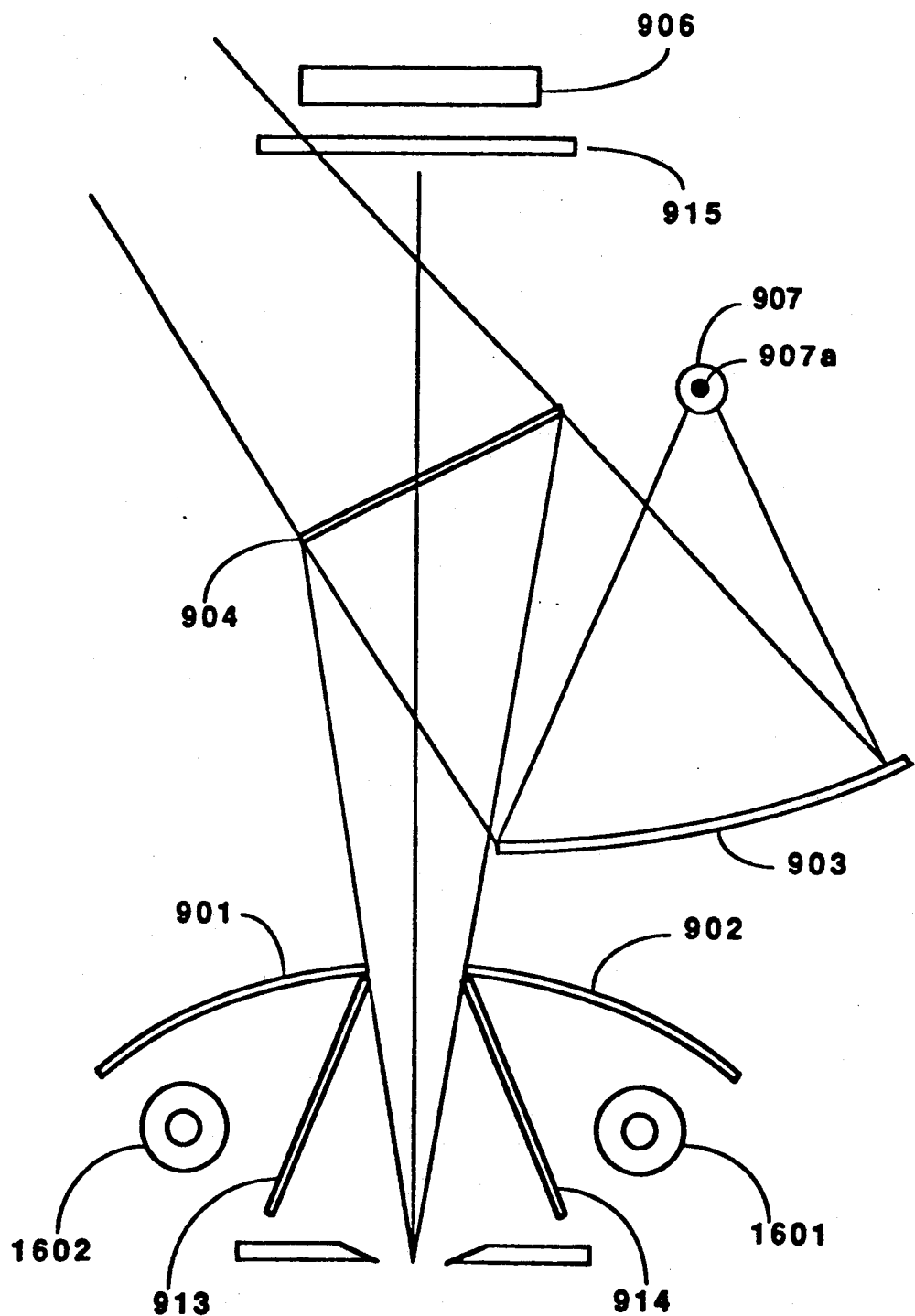

A second embodiment of the fluorescence illuminator of the present invention is illustrated schematically in FIG. 17. This embodiment is also adapted to provide efficient illumination of a substantially linear region 1601. It differs from the FIG. 16 system primarily in that a cylindrical lens 1604 has been used in place of mirrors 1504 and 1505. Light is brought to the system from a shortwave light source (not shown) by a single fiber bundle 1602 having an exit shape which, like that of bundles 1502 and 1503, is short in the plane of the shown cross section but of a width in the perpendicular direction that is approximately equal to the length of illuminated region 1601.

Beamsplitter 1612 is dichroic, which is to say that it is designed to be nearly 100% reflective at the short wavelength used to stimulate fluorescence, and nearly 100% transmissive at the longer wavelengths of the fluorescent light that is to be viewed.

Lens 1606 forms an image of region 1601 on a sensor, not shown, which may be a TDI sensor.

The requirement for entendue matching affects the size of lens 1604 in the same manner as it affected the size of mirrors 1504 and 1505.

End mirrors (not shown) are provided in the system of FIG. 17, for the same reason that they are provided in FIGS. 16a and 16b.

f. Combination illuminators.

The illuminator shown in FIG. 6 can be modified to operate in either fluorescence or visible mode. This is done as shown in FIG. 17b. The locations and nature of all components within this illuminator is essentially identical to the visible light illuminator shown in FIG. 6. The changes are as follows:

air cooled incandescent lamps 908 and 909 are replaced with water cooled mercury capillary arc lamps 1601 and 1602, and removable filters 913 and 914 are added. In addition, beamsplitter 904 is made removable.

filters 913 and 914 are inserted to block the visible light from lamps 1601 and 1602, allowing only the short wavelength light (less than 500 nm) to strike the substrate. When this illuminator is operating in fluorescence mode, lamp 907 is off, and filters 913, 914 and 915 are in place.

Filter 915 is a visible light filter which passes the fluorescent light and blocks the short wavelength light passed by filters 913 and 914.

When this illuminator is operating in quasi-Lambertian visible light mode, filters 913 and 914 are removed or exchanged for visible light filters, beamsplitter 904 is inserted, and lamp 907 is turned on.

This illuminator allows the inspection of a single substrate sequentially in visible mode and in fluorescence mode. The system then finds a separate set of defects in each mode, each set of defects, containing a certain proportion of "false" defects, (defects that are seen by the system but are really not there).

For instance, in visible mode, "false" defects may result from deep scratches in the copper or dark oxide patches on the copper, both of which might be seen as breaks in a trace. Similarly in fluorescence mode, a piece of dust lying across a trace might fluoresce resulting in the machine flagging a break.

Due to the very different nature of the visible and fluorescent imaging processes, the "false" defects generated by each inspection lie in nearly non-intersecting sets. Thus if the results of the two inspections are put through a logical operation that does not recognize a defect as real unless it is found by both inspections the greater portion of "false" defects is eliminated leaving nearly all real defects.

g. Black Oxide

The illuminator shown in FIG. 6 is well suited for inspection of bright copper traces. However, it is incapable of yielding a high contrast image on printed wiring boards in which the copper has been covered with an oxide layer, typically either black or brown.

In that case, the copper is nearly unreflective and appears dark except for an occasional bright spot where the oxide layer is not continuous. In actuality, the substrate (typically FR-4) appears brighter than the oxide covered copper.

In this variant of the basic invention this tendency of these substrates to appear brighter than the oxide is used to provide a high contrast image on which the FR4 substrate appears brighter than the traces.

Referring again to FIG. 9, it can be seen that the combination of high NA illumination and no slit produces quite bright FR4. The addition of high NA illumination does no appreciable brighten the oxide, so a high contrast image results in which the FR4 is brighter than the black oxide. To avoid specular reflections from occasional bright points on the copper (missing oxide) the upper lamp 907 is turned off and the beamsplitter 904 is withdrawn. The removal of the beamsplitter 904 is withdrawn. The removal of the beamsplitter provides an additional factor of two in the efficiency of collection of light from the remaining two lamps.

Thus the illuminator configuration used to inspect oxides on copper is identical to that shown in FIG. 6 except that the slit 910 and the beamsplitter 904 are removed.

h. Overall Optical System

Figure 18:
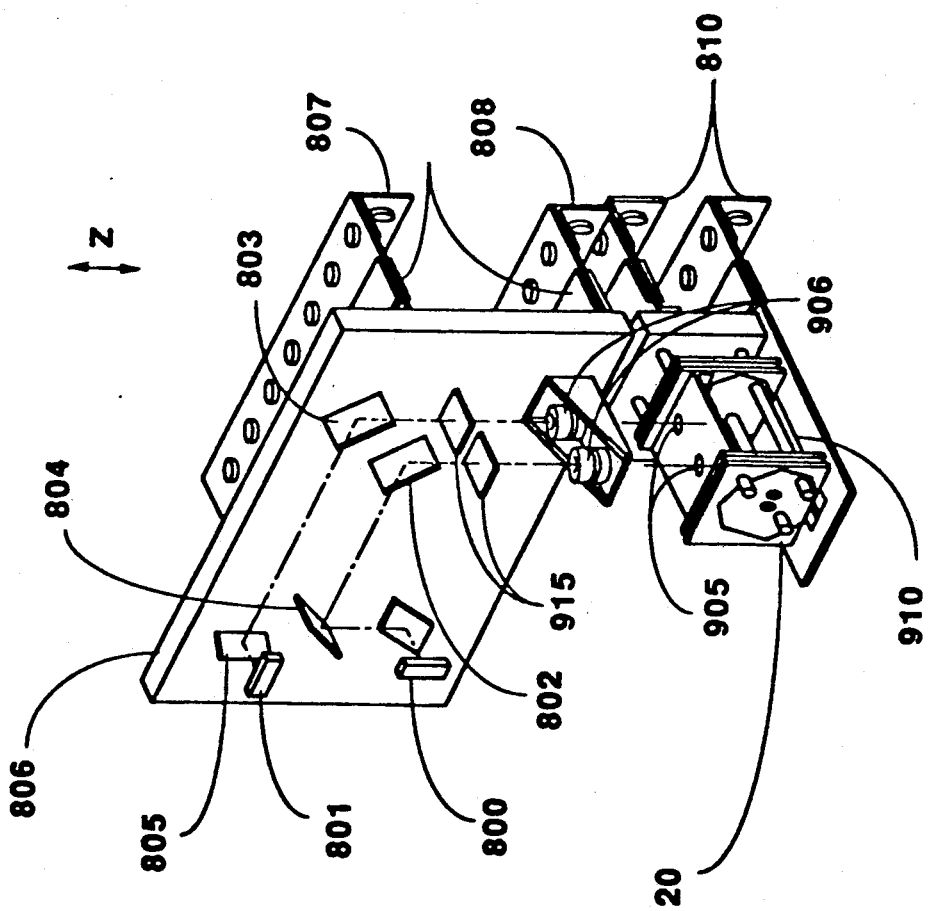
FIG. 18 is a perspective view illustrating the mechanical mounting of the slit assembly, the illuminator assembly, the sensor lenses, and the sensors with associated electronics with respect to each other.

In FIG. 18 the spatial relationships between the major elements of the optical system of the present invention are shown, with a configuration for inspecting two parallel paths on the surface to be inspected. While two optical viewing paths are shown here, any number of such paths from 1 to N could be provided. In should be obvious to those skilled in the optics art that the configuration could be expanded to inspect as many parallel paths at one time as desired. Throughout the remainder of the discussion herein for illuminator 20 only a single inspection path on the surface being inspected is addressed for simplicity.

In FIG. 18 there is shown an optics mounting plate 806 to which all of the components shown in this figure are mounted except for the slit assembly 910 and illuminator 20. Optics mounting plate 806 in turn is mounted to a fixed, relatively vibration free surface (not shown) by means of parallelogram flexure supports 807 and 808. These constrain the optics to move only in the vertical (z) direction for focussing. Similarly, slit assembly 910 is mounted below illuminator 20 of the same fixed, relatively vibration free surface (not shown) by means of flexible support 810. The slit assembly is mounted individually to the surface to permit it to fly on its integral air bearing above the surface to be inspected moving only in a vertical direction.

There is a LVDT sensor located between slit 910 and the optics plate 806 that senses the relative position of the two. The signal from the LVDT is used by a focussing servo that moves the optics plate 806 to focus the optics.

The illuminator 20 is also mounted to the same fixed surface to which the slit and optics plate are mounted. It is mounted via hinge supports 810. The illuminator is moved in a vertical direction to adjust for different board thicknesses. However, its depth of field is sufficient to allow it to remain fixed while a given batch of pwbs is inspected.

Beginning at the bottom of FIG. 18, there is shown a double long illuminator 20 having two viewing windows 905 in its upper plate. Above, and in alignment with viewing widows 905 are sensor lenses 906 and 906'. The image light path from each of lenses 906 and 906' extends upward to mirrors 802 and 803, respectively, where the image light path is turned through 452 remaining parallel to optics mounting plate 806. Each of the image light paths continue to mirrors 804 and 805, respectively. The upper path is turned through another 45° so that it is now perpendicular and extending out from mounting plate 806. The lower path is turned down and then out perpendicular to the plate. Each of the image light paths then arrive at their respective image sensor 800 and 801. By each of sensors 800 and 801 the image is converted into electrical signals which are processed by image processor 25.

TDI Sensor

A time delay integration (TDI) sensor is implemented by focusing a moving image onto a charge-coupled device (CCD) light sensing array. The CCD consists of a two-dimensional array of light-sensitive areas, or photosites. When photons enter a photosite, electrons are released. The electrons migrate to potential energy wells created by clock lines located on the face of the array. Once charge has accumulated in the photosites, it can be moved to adjacent photosites by changing the voltages on the clock lines. Repeated cycling of the clock lines moves the charge in a given photosite to a charge to voltage converter where it is read out of the sensor as a voltage.

TDI uses the fact that, as charge packets are transferred from photosite to photosite by cycling clock voltages as described above, the photosite will create electrons that add to the charge packet located at that photosite at the time. In TDI the charge packets are moved across the array so that, as a feature's image moves across the array, the charge generated by that feature is adding to the same charge packet. In effect, the array acts like a line sensor with an exposure time that is larger by a factor equal to the number of pixels in the TDI dimension.

The application of TDI to inspection is attractive because inspection processes tend to be light limited. The inspection rate of a line sensor is dictated by the signal-to-noise ratio needed and the amount of light available. Since the signal is proportional to the product of light power and time, if the light power is limited, the only way to get the needed signal-to-noise ratio is to increase the integration time, which lowers the inspection speed. Due to its pipeline structure, TDI allows the integration time to be increased without slowing down inspection. It also allows inspection with dark field illumination and fluorescence illumination, techniques that typically are light limited.

Figure 19:
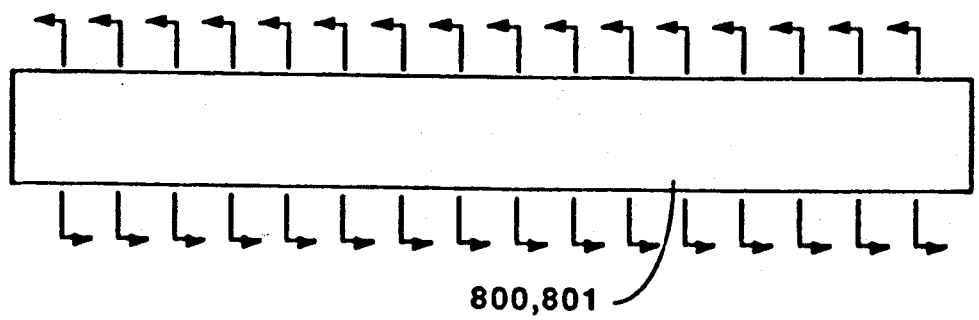
FIG. 19 is a schematic view of the multi-segment TDI sensor selected by the applicants for their particular application.
Figure 20:
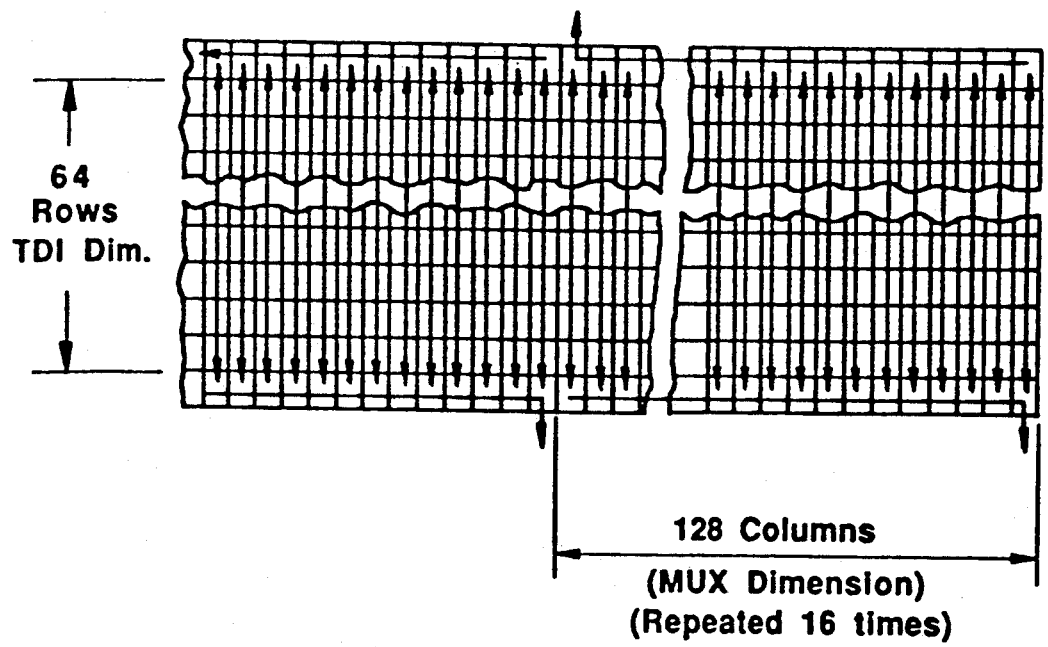
FIG. 20 is a more detailed view of the individual sensor segments of the TDI sensor of FIG. 20.
Figure 21A:
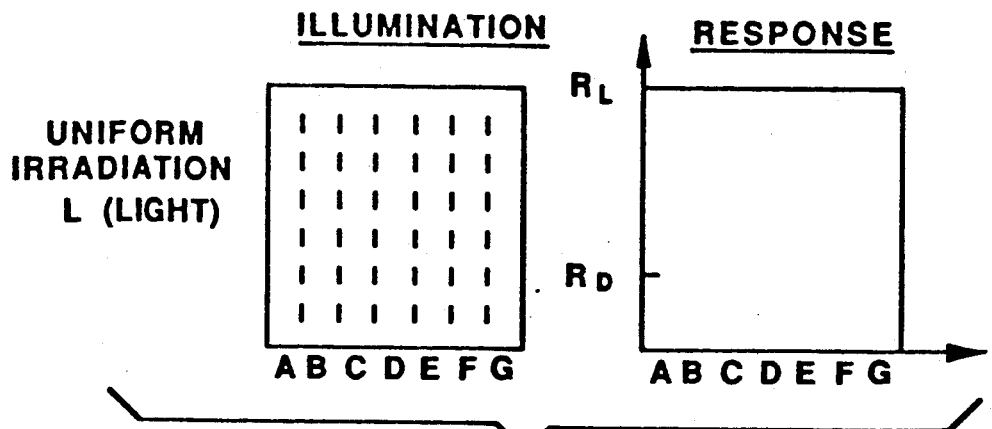
FIGS. 21a through 21j illustrate the modulation specification of the selected TDI sensor by showing the desired response to selected input illumination patterns.
Figure 21B:
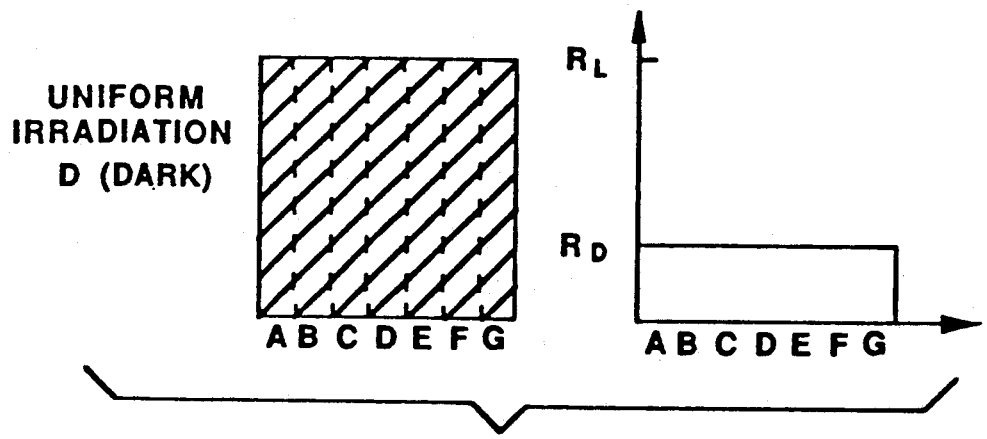
Figure 21C:
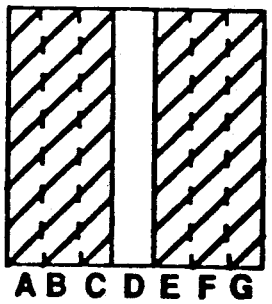
Figure 21C:
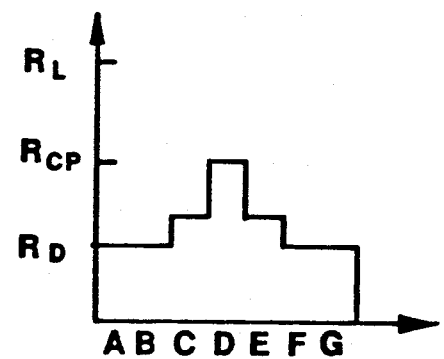
Figure 21D:
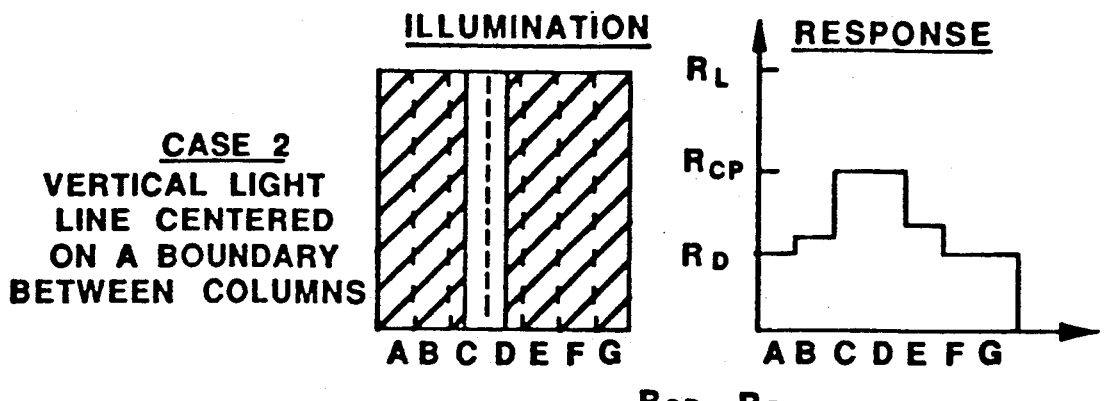
Figure 21E:
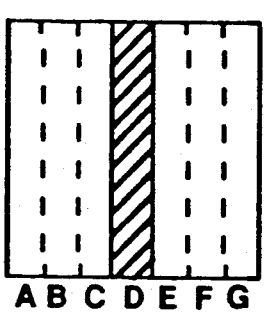
Figure 21E:
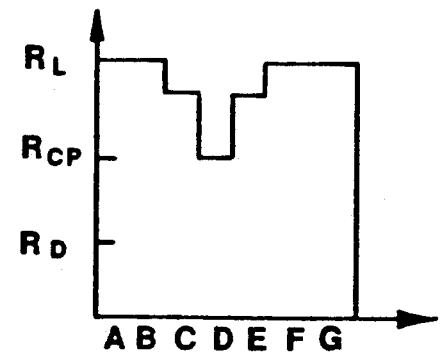
Figure 21F:
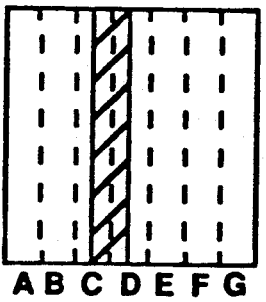
Figure 21F:
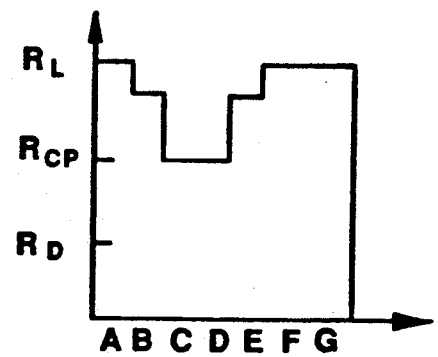
Figure 21G:
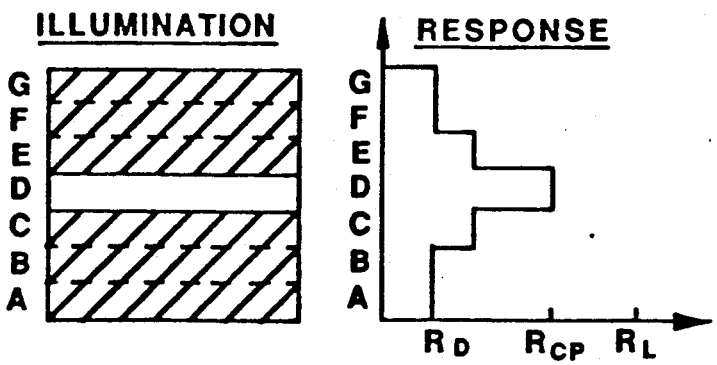
Figure 21H:
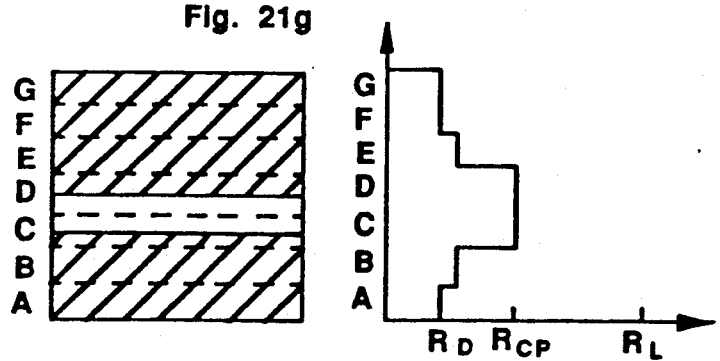
Figure 21I:
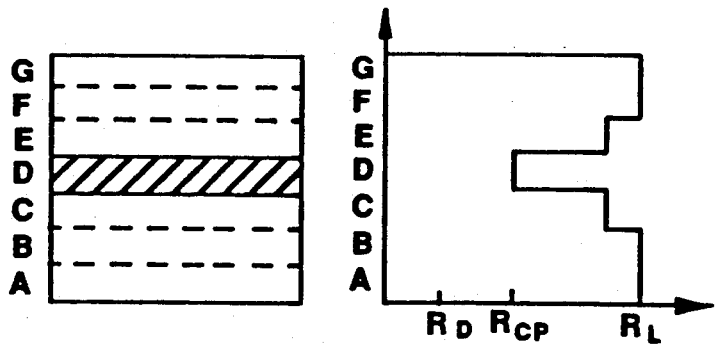
Figure 21J:
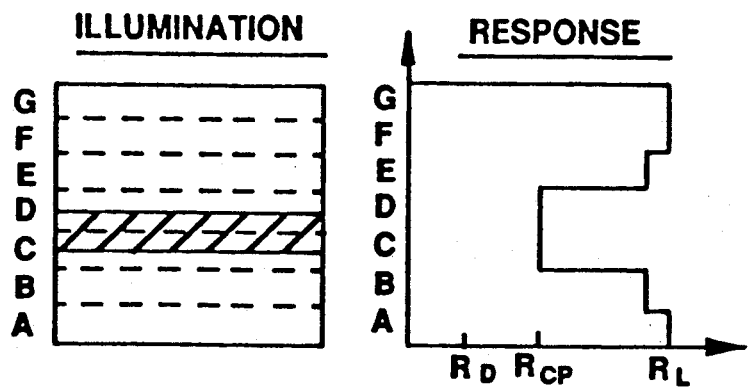

To keep the output rate of the sensor compatible with the high light collection rate, multiple output taps are used. This prevents the output data rate for each tap from becoming excessive. The particular TDI sensor configuration selected by the applicants for their application consists of sixteen segments as shown in FIG. 19. More specifically, the TDI sensor selected is a 64×2048 CCD image sensor having 64 rows in the TDI dimension and 2048 columns in the MUX dimension that is run in the time delay integration (TDI) mode as shown in FIG. 20.

In operation the columns shift up or down to serial shift registers at the top and bottom of the array. "Up" and "Down" refer to parallel shifts of a row in the TDI dimension. The serial shift registers have 16 taps, one every 128 elements. Each tap has an 8 MHz output data rate. The shift register at the top shifts left and the shift register at the bottom shifts right, looking at the front of the chip as shown in FIG. 19. Such a sensor uses 4-phase, buried channel, front illuminated construction. The specifications of the sensor selected by the applicants is as state above with an individual pixel size of 27×27 micrometers; an output sensitivity of 1u 230 v/e; a CTE of greater than 0.99995 at a line rate of 60K lines/sec., a data rate of 8 M pixels/sec. at a light level of 500K electrons; the dynamic range at the output being greater than 1250:1, saturated signal versus single pixel RMS noise, measured at 8 MHz clock rate with a minimum sample window of 15 ns; a dark current of less than 1% of saturation at 25° C. at an 8 Mhz pixel rate; and a column response non-uniformity of 10% within each tap and 15% tap to tap.

Figure 22:
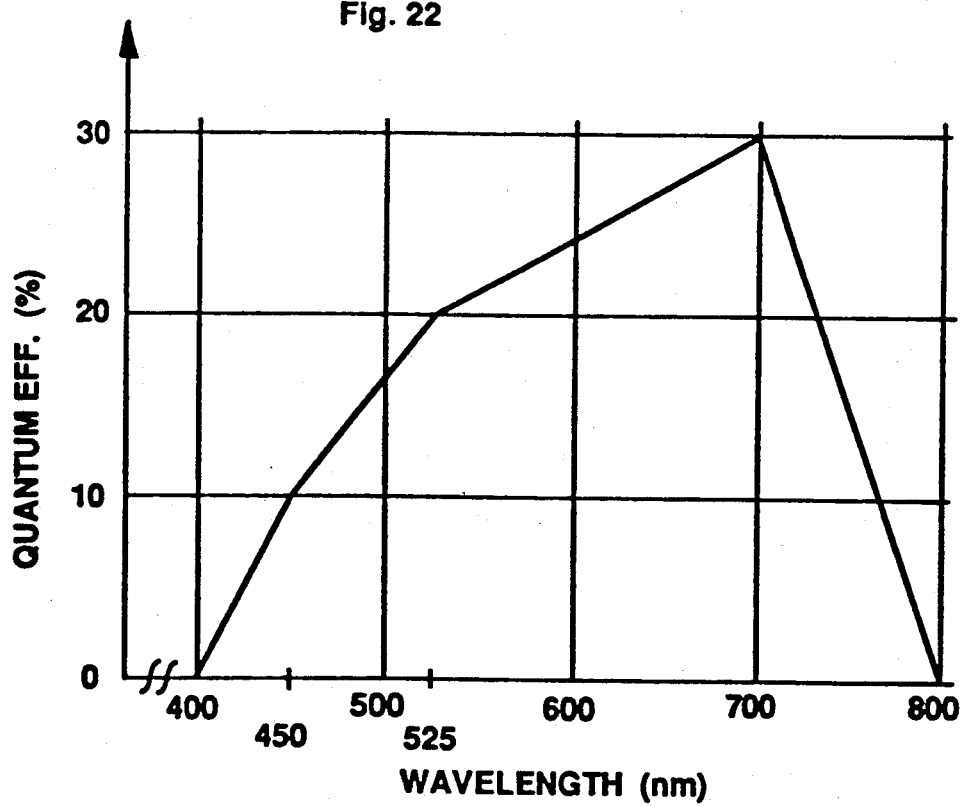
FIG. 22 is a graph of the minimum quantum efficiency versus wavelength of the selected TDI sensor.

Before continuing, several definitions are necessary. "Dark" and "light" lines are defined in terms of two irradiation levels, a "light" level L and a "dark" level D. When a large area is irradiated uniformly with level L, the response of each pixel is RL. When a large area is irradiated uniformly with level D, the response of each pixel is RD. For each of eight cases a line is defined as a spatial pattern of light levels L and D and the response of the pixels is specified in terms of RL and RD. FIGS. 21a through 21j provide the modulation specifications of the selected TDI sensor in graphical form. In each to these figures the response of the TDI sensor to different input illumination patterns are shown. To summarize the modulation specifications, when a single pixel-wide line is imaged onto the center row or column, the modulation as defined above (formula in FIG. 21c) must be greater than 60%. When it is imaged onto a boundary between rows or columns, the modulation must be greater than 40%. Similarly, FIG. 22 shows graphically the minimum acceptable QE (quantum efficiency) of the selected TDI sensor.

Figure 23:
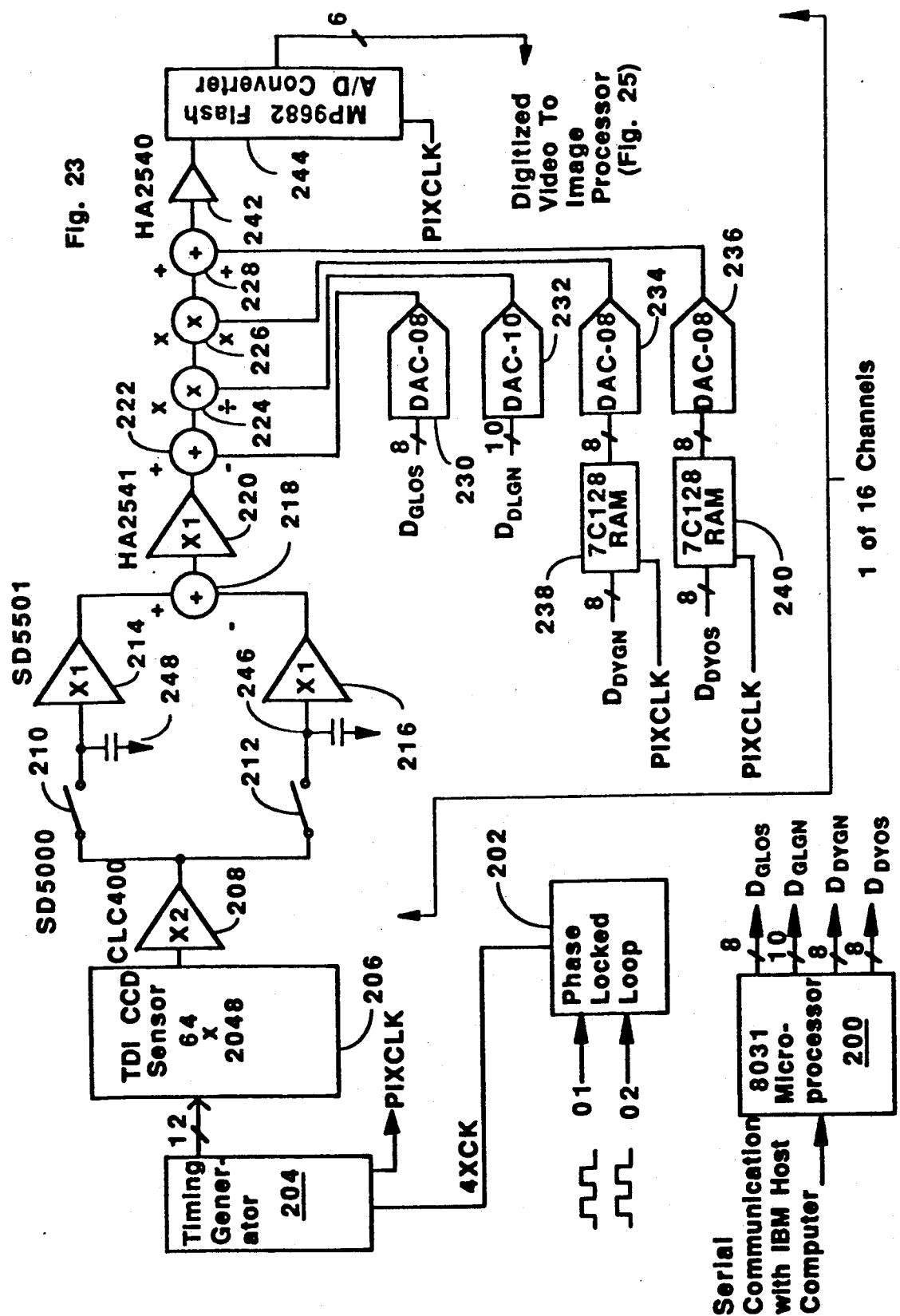
FIG. 23 is a block diagram of the TDI electronics for one section of the multi-section TDI sensor of the present invention.

FIG. 23 is a block diagram of the image pick-up electronics, including the TDI sensor 206, which corresponds to the sensor block 24 of FIG. 1. Included in the image pick-up electronics is a secondary processor 200 that, among other operations, generates four data words ($D_{GLOS}$, $D_{GLGN}$, $D_{DYGN}$, and $D_{DYOS}$) that provide input signals to the global gain and offset, and the dynamic gain and offset stage, for each segment of the TDI sensor, as discussed below. Also included is a phase locked loop 202, a timing generator 204 and the TDI sensor 206. For each segment of the TDI sensor 206, a separate and identical output circuit is provided of which only one of the 16 is shown in this figure. Each of those portions of the image pick-up electronics includes a factor of 2 multiplier 208, sampling switches 210 and 212, capacitors 246 and 248, buffers 214, 216, 220 and 242, adders 218, 222 and 228, multipliers 224 and 226, DACs 230-236, RAMs 238 and 240, and a flash A/D converter 244.

Sensor 206 has 16 segments, as discussed above, with a different output signal from each of those segments. In this figure the circuit for processing only one of those output signals is shown since each of the sensor output signals processing circuits are the same. The sensor output signal is first applied to a times two multiplier 208 to boost the signal, the amplified signal is then applied to the two sample and hold circuits. The upper sample and hold path (elements 210, 214 and 248) samples the signal pixel by pixel to eliminate clock and reset noise which occurs between pixels. The lower sample and hold path (elements 212, 216 and 246) samples the dark reference level which occurs during the line transfer time between each group of 128 pixels emerging from the sensor tap. The difference of these two signals is then generated by a differential amplifier (elements 218 and 220) resulting in a video signal which is substantially free of offset errors due to thermal or other changes in the dark output level of the sensor. That difference signal is then buffered by buffer 220 and applied to the cascade of adders 222 and 228 between which multipliers 224 and 226 are also cascaded. These elements, together with DACs 230-236 and RMAs 238 and 240, are the calibration circuitry. The function of this portion of the circuit is to remove anomalies in the image due to non-uniform illumination or non-uniform sensitivity of the sensor and provides a normalized signal at the output part of adder 228. The variations in the normalized signal should then only be the result of variations in the object being observed by the inspection system.

The calibration circuits provide correction for the global and dynamic gain and offset that might be present. The global gain and offset signals are dc signals that provide very large changes in the amplifier in order to accommodate widely varying objects that are being inspected by the system. For example, different types of pwbs have highly varying contrasts between the copper and the substrate or the photoresist and the substrate. Thus, it necessary to be able to vary the gain of the amplifier over a wide range in order to accommodate the possibility of inspecting any object that might be encountered. The input signals to DACs 230 and 232 are generated in response to signals from the host CPU 26 (FIG. 1) as it initially views the object to be inspected to insure that there is sufficient contrast to perform the inspection task.

The global calibration circuits provide for large changes in the gain and offset of all 16 channels simultaneously. This allows the host CPU to program the calibration circuits to accommodate a variety of inspectable objects whose background brightness and contrast may vary over wide ranges. The appropriate global gain and offset calibrations are determined empirically prior to the start of an inspection and remain constant during the inspection process.

The dynamic gain and offset circuitry does a pixel by pixel correction. The range of this circuitry is much restricted when compared to the global correction blocks. It can correct for up to ±20% variation in gain or offset, but it runs at a very high speed since it has to change every pixel. This is the circuitry that corrects for non-uniformities in the illumination or the response of the sensor 206. The way that it is calibrated is with an image of a "black" reference surface and a "white" reference surface that are located on the X-Y stage 12. Ideally the reference images should come out completely uniform, but they do not because of the non-uniformities. The host computer looks at what those responses are and then down loads appropriate corrections to processor 200 where the previously mentioned "D" signals are generated and applied to RAMs 238 and 240 to cause the correction of each of the pixels to the nominal value that they should have. The signal from buffer 220 is then corrected by subtracting the global offset therefrom, divided by the global gain correction, multiplied by the dynamic gain correction, and the dynamic offset is added thereto. The corrected signal from adder 228 is then applied to buffer 242 and then to flash A/D converter 244. The transfer function of the calibration circuits utilized in this application is as follows:

$$G.L = 44.74 - .100 D_{DYOS} + \quad (1)$$
$$(19.20 \times 10^6 (801.7 \times 10^{-6} + 1.578 \times 10^{-6} D_{DYGN})$$
$$(V_{IN} - 2.552 \times 10^{-3} D_{GLOS})/D_{GLGN})$$

where:
G.L = Gray level out of A/D converter (decimal) 0–63
$D_{DYOS}$ = Dynamic offset correction (decimal) 0–255
$D_{DYGN}$ = Dynamic gain correction (decimal) 0–255
$D_{GLOS}$ = Global offset correction (decimal) 0–255
$D_{GLGN}$ = Global gain correction (decimal) 100–1023
$V_{IN}$ = Analog output of sample and hold circuit (volts)

Figure 24:
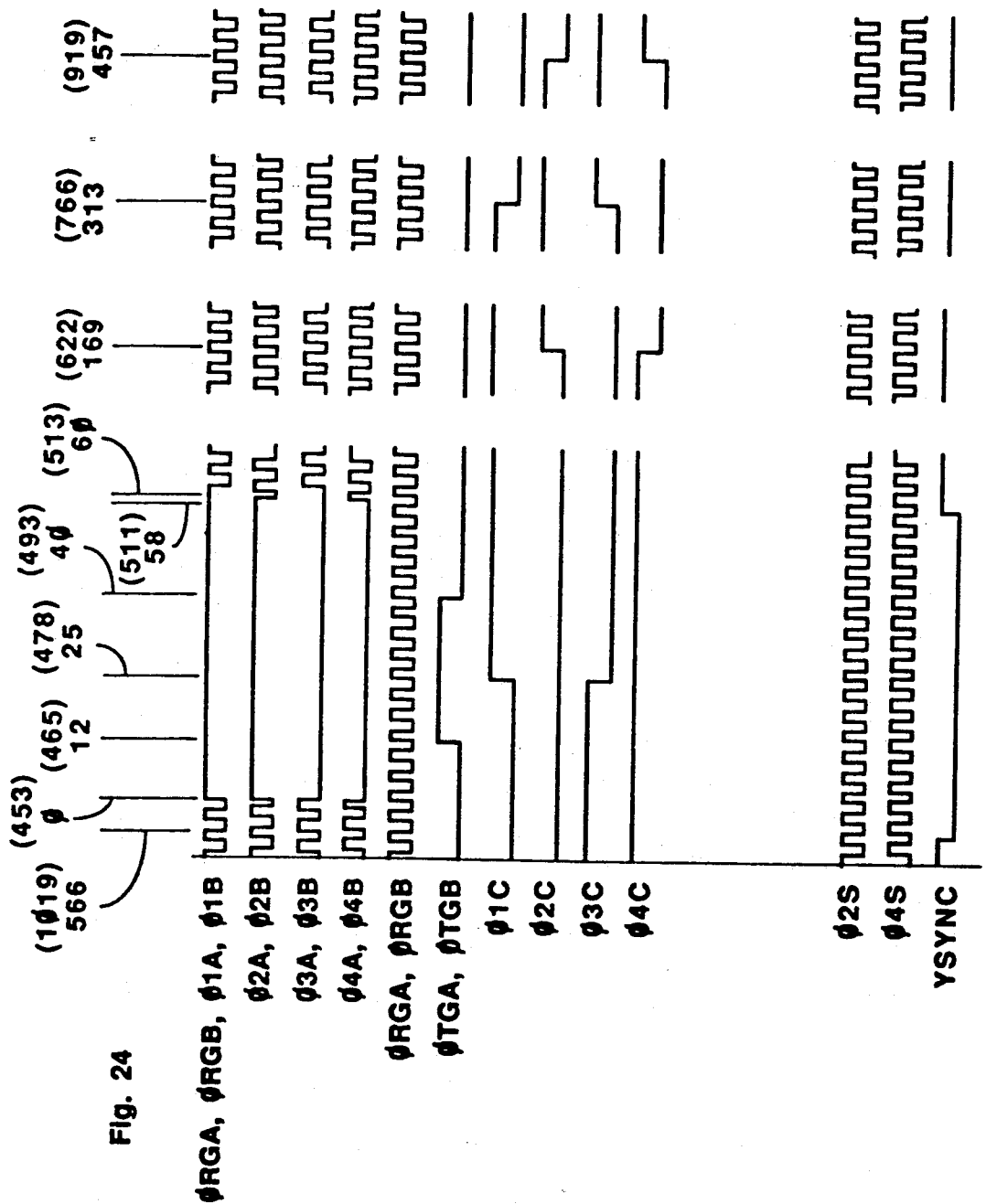
FIG. 24 is a timing diagram of selected signals from various blocks of the TDI electronics of FIG. 24.

Each segment of the TDI sensor 206 is controlled by phase locked loop circuit 202 via timing generator 204. The output signals required by the TDI sensor are shown in the timing diagram of FIG. 24. There are basically three classes of clock signals. There are the phase "C" clocks that shift charge in the TDI direction, and the phase "A" and "B" clocks that drive the output shift registers that shift the signals out of the array after it is imaged. Only one of the phase "A" or "B" clocks are active at any given time. Phase "C" clocks are free running clocks that are related to each other as shown in FIG. 24. As charge is shifted from the TDI section of the array, the optically sensitive section of the array, it is transferred to one of the two shift registers, the "A" or the "B" register and it is transferred out to each of the sixteen taps in the design of the present invention. The phase "A" and "B" clocks are the clocks that produce that charge transfer to the output charge to voltage converters. The phase "A" or "B" clocks are a four phase clock with each signal shifted sequentially 902 in phase from the previous one, thus the TDI sensor is referred to as a four phase device.

In addition to the phase "A" or "B" clocks that shift charge out of the array, there is also a reset gate clock and that is indicated as the phase "RGA" or "RGB" signals for the "A" and "B" registers, respectively. They are in essence free running clocks that reset the output amplifier on the sensor chip between each pixel to known levels. By looking at the encoder signals in the phase locked loop block 202 the direction that the X-Y stage 12 is moving in the X direction can be determined which thus, cause the selection of the appropriate one of the "A" and the "B" registers within sensor 206. The "A" and "B" registers are arranged on either side of the long axis of the array. The image is being moved across the array synchronously with the way that the signal charge is being moved across. To accommodate both scan directions it is necessary to shift charge in both directions therefore output registers are necessary on both sides of the array with only one of them active at anyone time. Thus, the direction in which the substrate is being scanned must agree with that being decoded in the phase locked loop 202.

Sensor 206 used in the application of the applicants is 2048 pixels long, and since there are sixteen taps on the array, those taps are placed every 128 pixels. When the phase "A" and "B" clocks are inactive signal charge is shifted in from the TDI section of the array. Then the phase "A" and "B" clocks, as necessary are initiated to shift out those 128 pixels per tap to the output amplifier for that tap. Then the clocks are again stopped and the next collection of pixels from the TDI section of the array are shifted in and the pattern is repeated. The periods when the "A" and the "B" phase clocks are inactive are defined as the transfer time. The TDI sensor collects data continuously and shifts the data out between the transfer times in bursts.

Across the top of the timing diagram of FIG. 24 are two series of numbers, one without parenthesis and the other set within parenthesis. Timing generator 204 in the implementation of the applicant's invention was implemented by binary counters driving a PROM which decodes the output signals from the counter and generates the timing signals shown in FIG. 24. The numbers in parenthesis are the counter output that corresponds to each increment in time in the timing diagram. The numbers not in parenthesis are arbitrary state assignments for each timing state in that cycle.

The $\phi_{2m}$ and $\phi_{4m}$ signals drive the sample and hold circuits, and the $Y_{sync}$ goes to the input buffer to synchronize the image computer with the data that is coming out.

The input signals to the phase locked loop 202 are shown in FIG. 23. Those signals are the biphase quadrature encoder signals which are a function of the speed of X-Y stage 12 and output signals from linear encoders 38 (FIG. 1). the pll 202 is programmable for the different stage speeds and pixel sizes. FIG. 28 describes the frequency of the output clock (4xck) for each combination of pixel size and scan (stage) speed that the applicants are using. A biphase quadrature encoder signal consists of two square wave for sinewave signals one of which lags the other by 90° of phase. When the scan direction changes, the signal that was lagging in the previous scan direction leads in the second scan direction.

Image Processor

Figure 25:
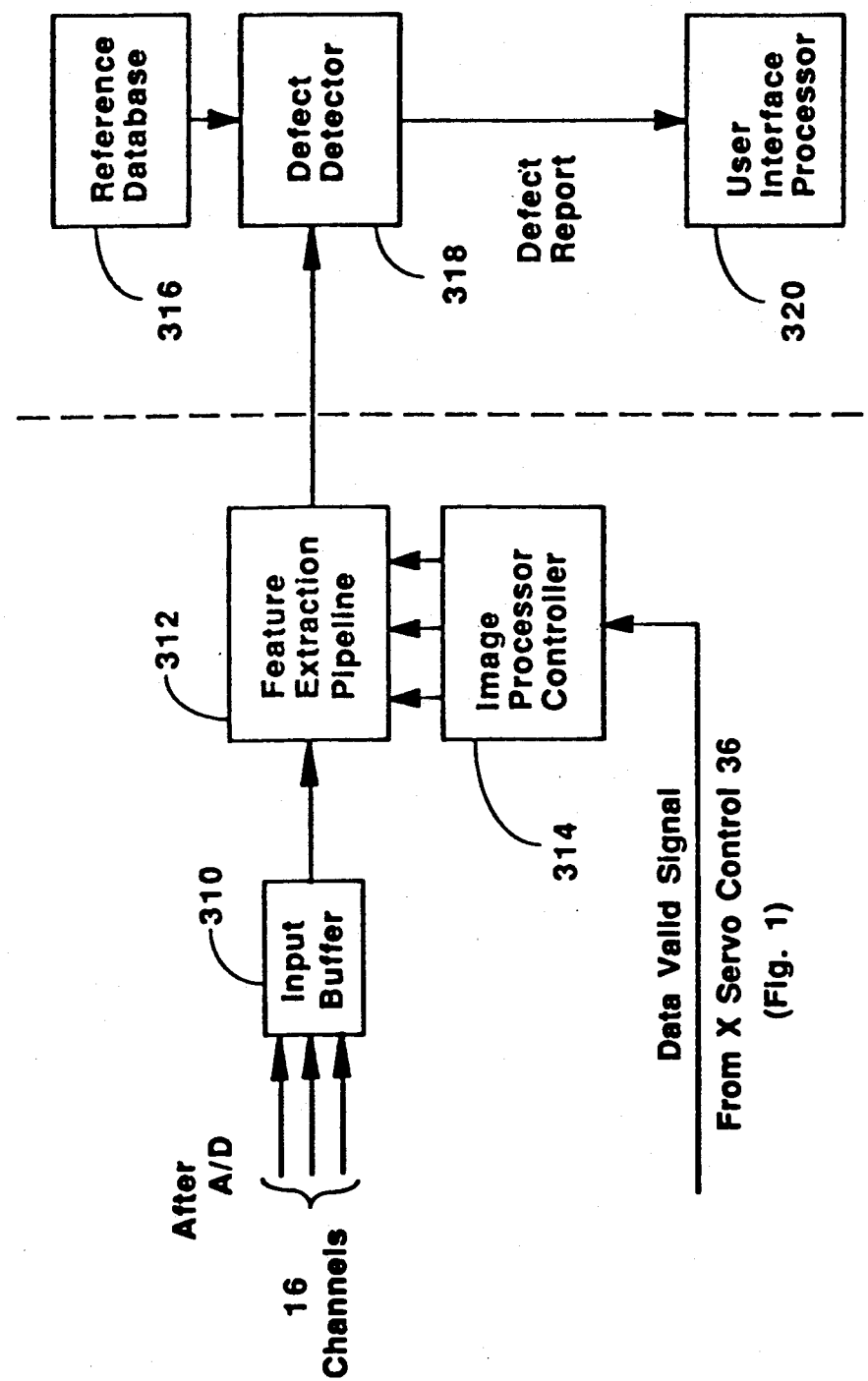
FIG. 25 is a block diagram of a single image processor electronics section which corresponds to one of the TDI electronics sections of FIG. 24 for use in the data base inspection configuration.

FIG. 25 is a block diagram of image processor 25 of FIG. 1 in the data base inspection configuration. The output signals from each of the A/D converters 244 of each of the sixteen sections of the image pick up electronics of FIG. 23 are applied in parallel to input buffer 310 in which a composite image signal is created. That composite image signal is then applied to the feature extraction pipeline 312 which, under the control of image processor controller 314, extracts the features from that signal and puts them into the same format as the feature information from the "golden board" which is stored in reference data base 316 (a portion of RAM 32 of FIG. 1). The features from data base 316 are then compared to the features from feature extraction pipeline 312 in defect detector 318 (could be performed by CPU 26 of FIG. 1). A defect report in which each detected defect is reported to the user interface processor 320 (could also be CPU 26 of FIG. 1) which informs the user of the detected defects. The output signal from input buffer 310 is also coupled to monitor 34 (FIG. 1 to display the region of the substrate being viewed by the user.

Figure 26:
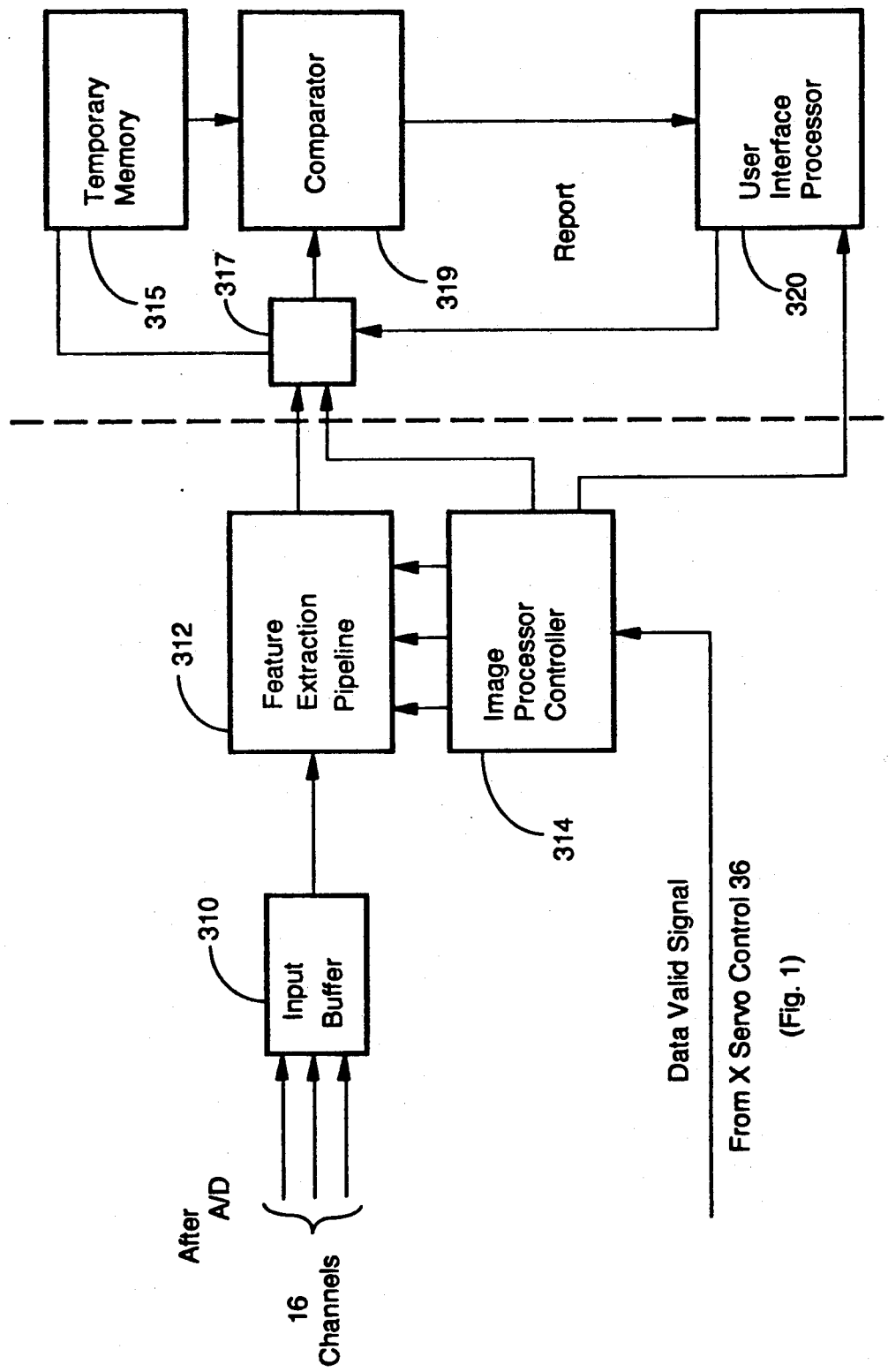
FIG. 26 is a block diagram of the processor electronics section which communicates with a single TDI sensor of FIG. 24 for pattern to pattern inspection.

FIG. 26 is a block diagram for performing die-to-die inspection using a single TDI sensor. To the left of the broken vertical line in FIG. 26 is the same as in FIG. 25. To the right of the vertical broken line there is temporary memory 315, switch 317, comparator 319 and user interface processor 320. In operation a first die is viewed by the TDI sensor with the feature of that die stored in temporary memory 315 via switch 317 which is controlled by image processor controller 314 and user interface processor 320. Where the characteristics of the first die have been stored in memory 315, those characteristics are applied to comparator 319 as the characteristics of a second die are also applied to comparator 319 via switch 317. Once the comparison is completed, a compare/non-compare signal is applied to user interface processor 320 where that signal is noted together with an indication from image processor controller 314 as to which pair of dice were being compared. The inspection continues with the characteristics of the second die being stored in temporary memory 315, etc.

By making memory 315 a FIFO (first in, first out) memory large enough to hold the characteristics of two die, switch 317 could be eliminated with the die characteristics being applied to memory 315 and comparator 319 simultaneously. In this embodiment, memory 315 is first initialized. Then the first die is inspected resulting in its characteristics being stored in memory 315 while they are compared to a null set of characteristics. This results in the expected non-compare signal from comparator 319. That being the start-up phase. Next, the characteristics of a second die are read into memory 315 while the characteristics of the first die are being written out simultaneously with the characteristics of the second die being applied to comparator 319. This process then continues as above for each of the dice to be inspected.

Figure 27:
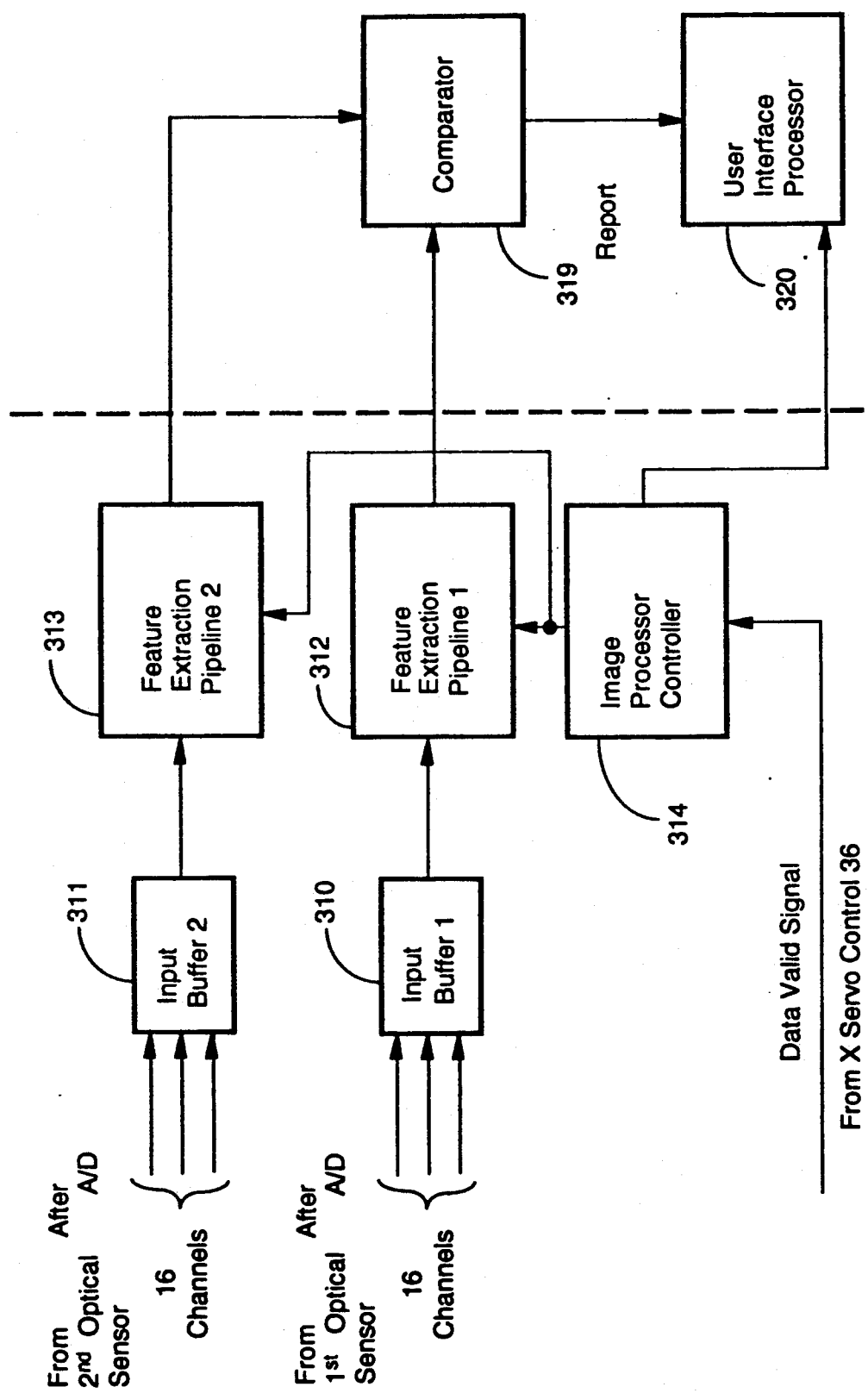
FIG. 27 is a block diagram of the processor electronics section which communicates simultaneously with a pair of TDI sensors of FIG. 24 for pattern to pattern inspection.

FIG. 27 is a block diagram for performing die-to-die inspection using a pair of TDI sensors. To the left of the broken vertical line there are the same elements in that location as in FIG. 26. Buffer 310 and feature extraction pipeline 312 constitute the path for processing the information from the first TDI sensor. A second buffer 311 and a second feature extraction pipeline 313 provide the path for processing the information from the second TDI sensor with pipeline 313 also under control of image processor controller 314. The output signals from pipeline 312 and 313 are simultaneously applied to comparator 319 which functions as described above in the discussion with respect to FIG. 26 as does user interface processor 320.

TABLE I

| $S_H$ | Pixel Size | Scan Speed | Pixel Size/Scan Speed Decode For PLL $S_H$ = PXS21 PXS20 SPD1 SPD0 | | | | | |
|---|---|---|---|---|---|---|---|---|
| | | | Endcoder Multiply | Feedback Devide | Output Devide | 4XCK | PIXCLK | Tach Clock |
| 0 | 6.5 μm | 3.05 ips | 4 | 1760 | 4 | 6.8 MHz | 1.7 MHz | .5 MHz |
| 1 | 6.5 | 6.1 | 2 | 1760 | 2 | 13.6 | 3.4 | 1.0 |
| 2 | 6.5 | 12.2 | 2 | 880 | 1 | 27.3 | 6.8 | 2.0 |
| N/A 3 | 6.5 | 24.4 | 1 | 880 | — | — | — | 4.0 |
| 4 | 13 | 3.05 | 4 | 1760 | 8 | 3.4 | .85 | .5 |
| 5 | 13 | 6.1 | 2 | 1760 | 4 | 6.8 | 1.7 | 1.0 |
| 6 | 13 | 12.2 | 2 | 880 | 2 | 13.6 | 3.4 | 2.0 |
| 7 | 13 | 24.4 | 1 | 880 | 1 | 27.3 | 6.8 | 4.0 |
| 8 | 26 | 3.05 | 4 | 1760 | 16 | 1.7 | .42 | .5 |
| 9 | 26 | 6.1 | 2 | 1760 | 8 | 3.4 | .85 | 1.0 |
| A | 26 | 12.2 | 2 | 880 | 4 | 6.8 | 1.7 | 2.0 |
| B | 26 | 24.4 | 1 | 880 | 2 | 13.6 | 3.4 | 4.0 |
| N/A C | — | 3.05 | 4 | 1760 | — | — | — | .5 |
| N/A D | — | 6.1 | 2 | 1760 | — | — | — | 1.0 |
| N/A E | — | 12.2 | 2 | 880 | — | — | — | 2.0 |
| N/A F | — | 24.4 | 1 | 880 | — | — | — | 4.0 |

What is claimed is:

1. Inspection apparatus for inspecting surface features of a substrate comprising:
   memory means for storing the desired features of the surface of the substrate from the CAD system that were used to produce the substrate;
   illumination means for substantially uniformly illuminating a region of the surface of the substrate to be inspected;
   TDI sensor means for imaging the region of the substrate illuminated by the illumination means; and
   comparison means responsive to the memory and sensor means for comparing the imaged region of the substrate with the stored desired features of the substrate.

2. A method for inspecting surface features of a substrate, said method comprising the steps of:
   a. storing the characteristics of the substrate from the CAD system that were used to produce the substrate into memory;
   b. illuminating for substantially uniformly illuminating a region of the surface of the substrate to be inspected;
   c. imaging the region of the substrate illuminated with a TDI sensor; and
   d. comparing the imaged region of the substrate with the stored desired features of the substrate.

3. A method for inspecting surface features of a substrate, said method comprising the steps of:
   a. illuminating by means of substantially uniform illumination at least a first die in a region of the surface of the substrate to be inspected;
   b. imaging a first die in the illuminated region of the substrate illuminated in step a. with a TDI sensor;
   c. storing the imaged die of step b.;
   d. illuminating by means of substantially uniform illumination at least a second die in a region of the surface of the substrate to be inspected;
   e. imaging a second die in the illuminated region of the substrate illuminated in step d. with a TDI sensor; and
   f. comparing the imaged second die of step e. with the image of the first die stored in step c.

4. A method as in claim 3 wherein said first and second dies are intended to be identical.

5. A method as in claim 4 wherein said first and second dies are on the same substrate.

6. A method as in claim 4 wherein said first and second dies are on different substrates.

7. A method as in claim 3 further including the steps of:
   g. storing the result of the comparison of step f. together with the locations of the first and second dies; and
   h. repeating steps a. through g. sequentially for each pair of dies with the second die in the previous pair becoming the first die and another die becoming the second die.

8. Inspection apparatus for inspecting surface features of a substrate comprising:
   illumination means for substantially uniform illumination of a first and second die in a region of the surface of at least one substrate to be inspected;
   TDI sensor means for sequentially imaging said first and second dies;
   memory means for storing the imaged first die as that die is imaged by said TDI sensor means; and
   comparison means responsive to the memory and TDI sensor means for comparing the imaged second die with the image of the first die stored in the memory means.

9. Inspection apparatus as in claim 8 wherein said first and second dies that are intended to be identical.

10. Inspection apparatus as in claim 9 wherein said first and second dies are on the same substrate.

11. Inspection apparatus as in claim 9 wherein said first and second dies are on different substrates.

12. Inspection apparatus as in claim 8 wherein said memory means also stores the result of the comparison together with the locations of the first and second dies.

* * * * *

(12) EX PARTE REEXAMINATION CERTIFICATE (5548th)
United States Patent
Chadwick et al.

(10) Number: US 5,131,755 C1
(45) Certificate Issued: Oct. 10, 2006

(54) AUTOMATIC HIGH SPEED OPTICAL INSPECTION SYSTEM

(75) Inventors: Curt H. Chadwick, Los Gatos, CA (US); Robert R. Sholes, Boulder Creek, CA (US); John D. Greene, Santa Cruz, CA (US); Francis D. Tucker, III, San Carlos, CA (US); Michael E. Fein, Mountain View, CA (US); P. C. Jann, Santa Clara, CA (US); David J. Harvey, Campbell, CA (US); William Bell, San Jose, CA (US)

(73) Assignee: KLA Instruments Corporation, San Jose, CA (US)

Reexamination Request:
No. 90/005,539, Oct. 25, 1999

Reexamination Certificate for:
Patent No.: 5,131,755
Issued: Jul. 21, 1992
Appl. No.: 07/429,859
Filed: Oct. 31, 1989

Related U.S. Application Data

(63) Continuation-in-part of application No. 07/158,289, filed on Feb. 19, 1989, now Pat. No. 4,877,326.

(51) Int. Cl.
 *G01B 11/30* (2006.01)

(52) U.S. Cl. .......................... 356/394; 356/446
(58) Field of Classification Search ...................... None
See application file for complete search history.

(56) References Cited

U.S. PATENT DOCUMENTS

| 3,763,348 A | 10/1973 | Costello | ..................... 219/347 |
| 3,909,602 A | 9/1975 | Micka | |

(Continued)

FOREIGN PATENT DOCUMENTS

| DE | 3422395 A1 | 1/1985 |
| EP | 0124113 A3 | 11/1984 |
| EP | 0129751 A3 | 1/1985 |
| EP | 0162120 A1 | 11/1985 |
| EP | 0294643 A2 | 12/1988 |

(Continued)

OTHER PUBLICATIONS

"Automatic Inspection System for Printed Circuit Boards," Y. Hara et al., *IEEE*, 1982, pp. 62–69.

(Continued)

*Primary Examiner*—Samuel A. Turner

(57) ABSTRACT

In each configuration, at least one TDI sensor is used to image substrate portions of interest, with those portions illuminated with substantially uniform illumination. In one configuration, a substrate is compared to prestored expected characteristic features. In a second configuration, first and second patterns in a region of the surface of at least one substrate are inspected by comparing one pattern against the other and noting whether they agree with each other. This is accomplished by illuminating the two patterns, imaging the first pattern and storing its characteristics in a temporary memory, then imaging the second pattern and comparing it to the stored characteristics from the temporary memory. Then the comparisons continue sequentially with the second pattern becoming the first pattern in the next imaging/comparison sequence against a new second pattern. Each time the comparison is performed, it is noted whether or not there has been agreement between the two patterns and which two patterns where compared. This inspection technique is useful for doing die-to-die inspections. A variation of the second configuration uses two TDI sensors to simultaneously image the first and second patterns, thus eliminating the need for temporary memory. In this configuration, the two patterns are simultaneously imaged and compared, then additional patterns are compared sequentially, in the same manner with the results of the comparisons and the pattern locations stored to determine which patterns are bad when the inspection of all patterns is completed.

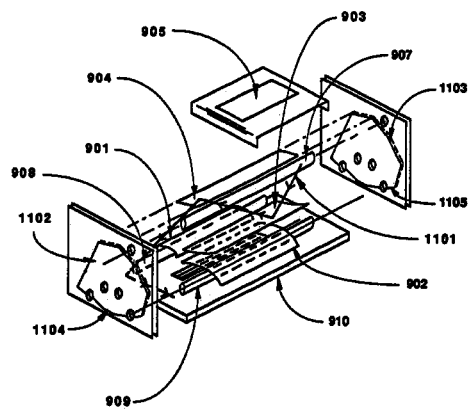

U.S. PATENT DOCUMENTS

| | | | |
|---|---|---|---|
| 3,957,031 A | 5/1976 | Winston | 126/270 |
| 3,963,354 A | 6/1976 | Feldman et al. | |
| 4,006,355 A | 2/1977 | Shemitz et al. | 240/51.11 R |
| 4,160,169 A | 7/1979 | Endicott et al. | |
| 4,247,203 A | 1/1981 | Levy et al. | 356/398 |
| 4,280,141 A | 7/1981 | McCann et al. | 358/213 |
| 4,347,001 A | 8/1982 | Levy et al. | 356/398 |
| 4,375,652 A | 3/1983 | White | |
| 4,421,410 A | 12/1983 | Karasaki | 356/378 |
| 4,449,818 A | 5/1984 | Yamaguchi et al. | 356/237 |
| 4,506,152 A | 3/1985 | Gupta | 250/216 |
| 4,510,616 A | 4/1985 | Lougheed et al. | 382/8 |
| 4,555,727 A | 11/1985 | Nun et al. | 358/106 |
| 4,614,430 A | 9/1986 | Hara et al. | 356/394 |
| 4,660,066 A | 4/1987 | Reid | |
| 4,680,627 A | 7/1987 | Sase et al. | |
| 4,692,690 A | 9/1987 | Hara et al. | 324/73 |
| 4,707,734 A | 11/1987 | Labinger et al. | 358/106 |
| 4,735,497 A | 4/1988 | Elterman | |
| 4,755,874 A | 7/1988 | Esrig et al. | |
| 4,761,681 A | 8/1988 | Reid | |
| 4,794,647 A | 12/1988 | Forgues et al. | 382/8 |
| 4,799,175 A | 1/1989 | Sano et al. | |
| 4,801,810 A | 1/1989 | Koso | 250/572 |
| 4,816,686 A | 3/1989 | Hara et al. | 250/458.1 |
| 4,845,558 A | 7/1989 | Tsai et al. | |
| 4,877,326 A | 10/1989 | Chadwick | |
| 4,926,489 A | 5/1990 | Danielson et al. | |
| 5,085,517 A | 2/1992 | Chadwick et al. | 356/394 |

FOREIGN PATENT DOCUMENTS

| | | |
|---|---|---|
| EP | 0369585 A1 | 5/1990 |
| GB | 2142444 A | 1/1985 |
| IL | 81450/2 | 2/1987 |
| JP | 55-57103 | 4/1980 |
| JP | 55-74409 | 6/1980 |
| JP | 55-89706 | 7/1980 |
| JP | 56-96204 | 8/1981 |
| JP | 57-95772 | 6/1982 |
| JP | 57-110913 | 7/1982 |
| JP | 57-194304 | 11/1982 |
| JP | 59180558 | 12/1984 |
| JP | 59-180558 | 12/1984 |
| JP | 59-220883 | 12/1984 |
| JP | 59-232344 | 12/1984 |
| JP | 60-27809 | 2/1985 |
| JP | 60-57929 | 4/1985 |
| JP | 60-61648 | 4/1985 |
| JP | 61102505 | 5/1986 |
| JP | 61-102505 | 5/1986 |
| JP | 61-273088 | 12/1986 |
| JP | 62-43505 | 2/1987 |
| JP | 62-247478 | 10/1987 |
| JP | 63-124939 | 5/1988 |
| JP | 63-136541 | 6/1988 |
| JP | 63-275129 | 11/1988 |
| JP | 63-311153 | 12/1988 |
| JP | 1-250847 | 10/1989 |
| JP | 3-160348 | 7/1991 |
| JP | 3-167456 | 7/1991 |

OTHER PUBLICATIONS

"The AOIs Have It Practical, automatic inspection of bare boards," W.M. Hastie, *Circuits Manufacturing*, Jan. 1986, pp. 22–23.

Product Brochure: Orbot PC–1100 Systems—Automatic Inspection of All Inner and Outer Layer PCBs, 1988, 6 pages.

"Time–Delay–And–Integration–Charge Coupled Devices (CCDs) Applied to the Thematic Mapper," L. L. Thompson et al., *SPIE*, vol. 143, *Applications of Electronic Imaging Systems*, 1978, pp. 19–26.

"A Time Delay and Integration CCD Image Sensor for High Speed and Low Light Level Scanning Applications," W.D. Washkurak et al., *CCD Image Sensors, Dalsa Inc. Databook*, 1989, pp. 198–201.

"Automatic Inspection of Mask Defects," P. Sandland, *SPIE*, vol. 100, Semiconductor Miorolithography 11, 1977, pp. 26–35.

*Principals of Optics*, $5^{th}$ Edition, 1974, Pergamon Press, Oxford, GB, pp. 522–524.

Vision 105 Manual.

Feb. '87 Nepcon Show Omni/CAD Brochure.

Corman, Stewart "Optical Inspection Technology for Multi–Layer Printed Wiring Boards", Test & Measurement World, May 1983.

Hastle, William M. "The AOIs Have It" Circuits Manufacturing, Jan. 1986, p. 22–23.

Thompson et al "Time–Delay–and Integration Charge Coupled Devices Applied to the Thematic Mapper" SPIE vol. 143 Applications of Electronic Imaging Systems (1978) p. 19–26.

Quekett, John, "A Practical Treatise on the Use of the Microscope", London (1848) p. 40–46, 98–189.

Restrick, Robert "An Automatic Optical Printed Circuit Inspection System" SPIE vol. 116 Solid State Imaging Devices (1977) p. 76–81.

Hooke, R. "Micrographia: Or Some Physiological Descriptions of Minute Bodies Made by Magnifying Glasses w/Observations and Inquiries Thereupon" London, Nov. 1664.

McCormick, J.B. "Eighteenth Century Microscopes", Science Heritage Ltd. (1987) p. 20–25.

Hara, Yasuhiko "Automatic Inspection System for Printed Circuit Boards", Conference Record 1982 Workshop On Industrial Applications of Machine Vision, May 3–5, 1982, p. 62–70.

Strope et al "Optical Inspection System" IBM Technical Disclosure Bulletin, vol. 23 No. 9, Feb. 1981 p. 4076–4077.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3 and 8 are determined to be patentable as amended.

Claims 4–7 and 9–12, dependent on an amended claim, are determined to be patentable.

New claims 13–110 are added and determined to be patentable.

1. Inspection apparatus for inspecting surface features of a substrate comprising:
   memory means for storing the desired features of the surface of the substrate from [the] *a* CAD system that [were] *was* used to produce the substrate;
   illumination means for substantially uniformly illuminating a region of the surface of the substrate to be inspected;
   TDI sensor means for imaging the region of the substrate illuminated by the illumination means; and
   comparison means responsive to the memory and sensor means for comparing the imaged region of the substrate with the stored desired features of the substrate *to detect defects of the substrate.*

2. A method for inspecting surface features of a substrate, said method comprising the steps of:
   a. storing the characteristics of the substrate from [the] *a* CAD system that [were] *was* used to produce the substrate into memory;
   b. illuminating for substantially uniformly illuminating a region of the surface of the substrate to be inspected;
   c. imaging the region of the substrate illuminated with a TDI sensor; and
   d. comparing the imaged region of the substrate with the stored desired features of the substrate *to detect defects of the substrate.*

3. A method for inspecting surface features of a substrate, said method comprising the steps of:
   a. illuminating by means of substantially uniform illumination at least a first die in a region of the surface of the substrate to be inspected;
   b. imaging a first die in the illuminated region of the substrate illuminated in step a. with a TDI sensor;
   c. storing the imaged die of step b.;
   d. illuminating by means of substantially uniform illumination at least a second die in a region of the surface of the substrate to be inspected;
   e. imaging a second die in the illuminated region of the substrate illuminated in step d. with a TDI sensor; and
   f. comparing the imaged second die of step e. with the image of the first die stored in step c *to detect defects of the substrate.*

8. Inspection apparatus for inspecting surface features of a substrate comprising:
   illumination means for substantially uniform illumination of a first and second die in a region of the surface of at least one substrate to be inspected;
   TDI sensor means for sequentially imaging said first and second dies;
   memory means for storing the imaged first die as that die is imaged by said TDI sensor means; and
   comparison means responsive to the memory and TDI sensor means for comparing the imaged second die with the image of the first die stored in the memory means *to detect defects of the substrate.*

13. *The apparatus of claim 1, wherein said TDI sensor means is bidirectional and images the region of the substrate illuminated by the illumination means along either direction of a predetermined axis.*

14. *The apparatus of claim 13, wherein said TDI sensor means includes a sensor array and shift register circuits on both sides of the array along an aixs of the array.*

15. *The apparatus of claim 13, wherein the TDI sensor means images the region along a scanning direction, said apparatus further comprising an instrument that causes the TDI sensor means to shift signals in a direction that corresponds to the scanning direction.*

16. *The apparatus of claim 15, further comprising:*
   *an X-Y stage that provides movement to said substrate; and*
   *a direction sensor detecting the direction of motion of said X-Y stage and developing a direction signal corresponding to said direction of motion.*

17. *The apparatus of claim 16, said instrument comprising a phase locked loop responsive to said direction signal from said direction sensor to control shifting of signals by said TDI sensor.*

18. *The apparatus of claim 1, further comprising a device sampling an output of the TDI sensor means to determine a dark reference level of the sensor means.*

19. *The apparatus of claim 18, said device also deriving a difference signal between an output of the TDI sensor means and the dark reference level.*

20. *The apparatus of claim 1, further comprising a circuit providing a correction for global or dynamic gain to an output of the TDI sensor means.*

21. *The apparatus of claim 20, wherein said circuit provides said correction based upon calibrations prior to the imaging of the region by the TDI sensor means.*

22. *The apparatus of claim 1, further comprising a circuit providing a correction for global or dynamic offset to an output of the TDI sensor means.*

23. *The apparatus of claim 22, wherein said circuit provides said correction based upon calibrations prior to the imaging of the region by the TDI sensor means.*

24. *The method of claim 2, wherein said TDI sensor means is bidirectional and has two selectable directions for shifting and accumulating signals; said method further comprising:*
   *e. displacing the substrate relative to said bidirectional TDI sensor means along either direction of a predetermined axis;*
   *f. sensing the relative movement of said substrate along said predetermined axis;*
   *g. generating signals to select one of said selectable directions of said bidirectional TDI sensor depending upon the direction of relative movement along the predetermined axis.*

25. The method of claim 2, further comprising an output of the TDI sensor means to determine a dark reference level of the sensor means.

26. The method of claim 25, further comprising deriving a difference signal between an output of the TDI sensor means and the dark reference level.

27. The method of claim 2, further comprising providing a correction for global or dynamic gain to an output of the TDI sensor means.

28. The method of claim 27, wherein said providing step includes said correction based upon calibrations prior to the imaging of the region with the TDI sensor means.

29. The method of claim 2, further comprising providing a correction for global or dynamic offset to an output of the TDI sensor means.

30. The method of claim 29, wherein said providing step includes said correction based upon calibrations prior to the imaging of the region by the TDI sensor means.

31. The apparatus of claim 8, wherein said TDI sensor means is bidirectional and images the region of the substrate illuminated by the illumination means along either direction of a predetermined axis.

32. The apparatus of claim 31, wherein said TDI sensor means includes a sensor array and shift register circuits on both sides of the array along an aixs of the array.

33. The apparatus of claim 31, wherein the TDI sensor means images the region along a scanning direction, said apparatus further comprising an instrument that causes the TDI sensor means to shift signals in a direction that corresponds to the scanning direction.

34. The apparatus of claim 33, further comprising:
an X-Y stage that provides movement to said substrate; and
a direction sensor detecting the direction of motion of said X-Y stage and developing a direction signal corresponding to said direction of motion.

35. The apparatus of claim 34, said instrument comprising a phase locked loop responsive to said direction signal from said direction sensor to control shifting of signals by said TDI sensor.

36. The apparatus of claim 8, further comprising a device sampling an output of the TDI sensor means to determine a dark reference level of the sensor means.

37. The apparatus of claim 36, said device also deriving a difference signal between an output of the TDI sensor means and the dark reference level.

38. The apparatus of claim 8, further comprising a circuit providing a correction for global or dynamic gain to an output of the TDI sensor means.

39. The apparatus of claim 38, wherein said circuit provides said correction based upon calibrations prior to the imaging of the region by the TDI sensor means.

40. The apparatus of claim 8, further comprising a circuit providing a correction for global or dynamic offset to an output of the TDI sensor means.

41. The apparatus of claim 40, wherein said circuit provides said correction based upon calibrations prior to the imaging of the region by the TDI sensor means.

42. The apparatus of claim 8, said TDI sensor means including two TDI sensors for imaging said two dies respectively.

43. The method of claim 3, wherein said TDI sensor means is bidirectional and has two selectable directions for shifting and accumulating signals; said method further comprising:
g. displacing the substrate relative to said bidirectional TDI sensor means along either direction of a predetermined axis;
h. sensing the relative movement of said substrate along said predetermined axis;
i. generating signals to select one of said selectable directions of said bidirectional TDI sensor depending upon the direction of relative movement along the predetermined axis.

44. The method of claim 3, further comprising an output of the TDI sensor means to determine a dark reference level of the sensor means.

45. The method of claim 44, further comprising deriving a difference signal between an output of the TDI sensor means and the dark reference level.

46. The method of claim 3, further comprising providing a correction for global or dynamic gain to an output of the TDI sensor means.

47. The method of claim 46, wherein said providing step includes said correction based upon calibrations prior to the imaging of the region with the TDI sensor means.

48. The method of claim 3, further comprising providing a correction for global or dynamic offset to an output of the TDI sensor means.

49. The method of claim 48, wherein said providing step includes said correction based upon calibrations prior to the imaging of the region by the TDI sensor means.

50. The method of claim 3, wherein steps b. and e. employ different TDI sensors.

51. Inspection apparatus for inspecting surface features of a substrate comprising:
an X-Y stage to provide movement to said substrate mounted thereon;
location sensor means for detecting the location of said X-Y state and developing a signal corresponding to said location;
memory means for storing desired features of the surface of the substrate from a CAD system that was used to produce the substrate;
illumination means for substantially uniformly illuminating a region of the surface of the substrate to be inspected;
a bidirectional TDI sensor means for imaging the region of the substrate illuminated by the illumination means along either direction of a predetermined axis;
a phase locked loop responsive to said location signal from said location sensor means to control said TDI sensor; and
comparison means responsive to the memory and sensor means for comparing the imaged region of the substrate with the stored desired features of the substrate to detect defects of the substrate.

52. A method for inspecting surface features of a substrate, said method comprising the steps of:
a. storing desired features of the surface of the substrate from a CAD system that was used to produce the substrate into memory;
b. illuminating for substantially uniformly illuminating a region of the surface of the substrate to be inspected;
c. imaging the region of the substrate illuminated means with a bidirectional TDI sensor means having a selectable output means;
d. displacing the substrate relative to said bidirectional TDI sensor means along either direction of a predetermined axis;
e. sensing the relative movement of said substrate along said predetermined axis;
f. generating signals to select said selectable output means of said bidirectional TDI sensor depending upon the direction of relative movement along the predetermined axis; and g. comparing the imaged region of the substrate with the stored desired features of the substrate to detect defects of the substrate.

53. A method for inspecting surface features of a substrate, said method comprising the steps of:
   a. illuminating by means of substantially uniform illumination at least a first die in a region of the surface of the substrate to be inspected;
   b. imaging a first die in the illuminated region of the substrate illuminated in step a. with a TDI sensor;
   c. storing the imaged die of step b.;
   d. illuminating by means of substantially uniform illumination at least a second die in a region of the surface of the substrate to be inspected;
   e. imaging a second die in the illuminated region of the substrate illuminated in step d. with a bidirectional TDI sensor having a selectable output means;
   f. displacing the substrate relative to said bidirectional TDI sensor means along either direction of a predetermined axis;
   g. sensing the relative movement of said substrate along said predetermined axis;
   h. generating signals to select said selectable output means of said bidirectional TDI sensor depending upon the direction of relative movement along the predetermined axis; and
   i. comparing the imaged second die of step e. with the image of the first die stored in step c.

54. A method as in claim 53 further including the steps of:
   j. storing the result of the comparison of step i. together with the locations of the first and second dies; and
   k. repeating steps a. through j. sequentially for each pair of dies with the second die in the previous pair becoming the first die and another die becoming the second die.

55. Inspection apparatus for inspecting surface features of a substrate comprising:
   an X-Y stage to provide movement to said substrate mounted thereon;
   location sensor means for detecting the location of said X-Y stage and developing a signal corresponding to said location;
   illumination means for substantially uniform illumination of a first and second die in a region of the surface of at least one substrate to be inspected;
   a bidirectional TDI sensor means for sequentially imaging said first and second dies along either direction of a predetermined axis;
   memory means for storing the imaged first die as that die is imaged by said TDI sensor means;
   a phase locked loop responsive to said location signal from said location sensor means to control said TDI sensor; and
   comparison means responsive to the memory and TDI sensor means for comparing the imaged second die with the image of the first die stored in the memory means.

56. The inspection apparatus of claim 1 wherein the illumination comprises simultaneous illumination of multiple points on the substrate.

57. The inspection apparatus of claim 56 wherein the illumination comprises brightfield illumination.

58. The inspection apparatus of claim 56 wherein the illumination comprises darkfield illumination.

59. The inspection apparatus of claim 56 wherein the illumination comprises both darkfield and brightfield illumination.

60. The inspection apparatus of claim 1 wherein the illumination comprises brightfield illumination.

61. The inspection apparatus of claim 1 wherein the illumination comprises darkfield illumination.

62. The inspection apparatus of claim 1 wherein the illumination comprises both darkfield and brightfield illumination.

63. The inspection apparatus of claim 1 wherein the illumination is suitable for inspection in fluorescence mode.

64. The inspection apparatus of claim 1 which further includes a calibration circuit to provide correction for gain.

65. The inspection apparatus of claim 1 which further includes a calibration circuit to provide correction for offset.

66. The inspection apparatus of claim 1 which further includes a calibration circuit to provide correction for gain and offset.

67. The inspection apparatus of claim 1 which further includes means for changing the scan direction.

68. The inspection apparatus of claim 1 wherein the TDI sensor means includes multiple TDI sensors that operate simultaneously.

69. The method for inspecting of claim 2 wherein the illumination comprises simultaneous illumination of multiple points on the substrate.

70. The method for inspecting of claim 69 wherein the illumination comprises brightfield illumination.

71. The method for inspecting of claim 69 wherein the illumination comprises darkfield illumination.

72. The method for inspecting of claim 69 wherein the illumination comprises both darkfield and brightfield illumination.

73. The method for inspecting of claim 2 wherein the illumination comprises brightfield illumination.

74. The method for inspecting of claim 2 wherein the illumination comprises darkfield illumination.

75. The method for inspecting of claim 2 wherein the illumination comprises both darkfield and brightfield illumination.

76. The method for inspecting of claim 2 wherein the illumination is suitable for inspection in fluorescence mode.

77. The method for inspecting of claim 2 which further includes a calibration circuit to provide correction for gain.

78. The method for inspecting of claim 2 which further includes a calibration circuit to provide correction for offset.

79. The method for inspecting of claim 2 which further includes a calibration circuit to provide correction for gain and offset.

80. The method for inspecting of claim 2 which further includes means for changing the scan direction.

81. The inspection apparatus of claim 2 wherein the TDI sensor means includes multiple TDI sensors that operate simultaneously.

82. The method for inspecting of claim 3 wherein the illumination comprises simultaneous illumination of multiple points on the substrate.

83. The method for inspecting of claim 82 wherein the illumination comprises brightfield illumination.

84. The method for inspecting of claim 82 wherein the illumination comprises darkfield illumination.

85. The method for inspecting of claim 82 wherein the illumination comprises both darkfield and brightfield illumination.

86. The method for inspecting of claim 3 wherein the illumination comprises brightfield illumination.

87. The method for inspecting of claim 3 wherein the illumination comprises darkfield illumination.

88. The method for inspecting of claim 3 wherein the illumination comprises both darkfield and brightfield illumination.

89. The method for inspecting of claim 3 wherein the illumination is suitable for inspection in fluorescence mode.

90. The method for inspecting of claim 3 which further includes a calibration circuit to provide correction for gain.

91. The method for inspecting of claim 3 which further includes a calibration circuit to provide correction for offset.

92. The method for inspecting of claim 3 which further includes a calibration circuit to provide correction for gain and offset.

93. The method for inspecting of claim 3 which further includes means for changing the scan direction.

94. The inspection apparatus of claim 3 wherein the TDI sensor means includes multiple TDI sensors that operate simultaneously.

95. The inspection apparatus of claim 8 wherein the illumination comprises simultaneous illumination of multiple points on the substrate.

96. The inspection apparatus of claim 95 wherein the illumination comprises brightfield illumination.

97. The inspection apparatus of claim 95 wherein the illumination comprises darkfield illumination.

98. The inspection apparatus of claim 95 wherein the illumination comprises both darkfield and brightfield illumination.

99. The inspection apparatus of claim 8 wherein the illumination comprises brightfield illumination.

100. The inspection apparatus of claim 8 wherein the illumination comprises darkfield illumination.

101. The inspection apparatus of claim 8 wherein the illumination comprises both darkfield and brightfield illumination.

102. The inspection apparatus of claim 8 wherein the illumination is suitable for inspection in fluorescence mode.

103. The inspection apparatus of claim 8 which further includes a calibration circuit to provide correction for gain.

104. The inspection apparatus of claim 8 which further includes a calibration circuit to provide correction for offset.

105. The inspection apparatus of claim 8 which further includes a calibration circuit to provide correction for gain and offset.

106. The inspection apparatus of claim 8 which further includes means for changing the scan direction.

107. The inspection apparatus of claim 8 wherein the TDI sensor means includes multiple TDI sensors that operate simultaneously.

108. The apparatus of claim 1, said illumination means focusing radiation to the region of the substrate, said apparatus further comprising optics focusing radiation from the region to the TDI sensor means.

109. The method of claim 2, wherein said illuminating comprises focusing radiation to the region of the surface of the substrate to illuminate the region, and said imaging comprises focusing radiation from the region to the TDI sensor means.

110. The apparatus of claim 8, said illumination means focusing radiation to the region of the substrate, said apparatus further comprising optics focusing radiation from the region to the TDI sensor means.

\* \* \* \* \*